United States Patent
Gorelik et al.

(10) Patent No.: US 11,471,225 B2
(45) Date of Patent: Oct. 18, 2022

(54) SEMI-AUTOMATIC PRECISION POSITIONING ROBOT APPARATUS AND METHOD

(71) Applicant: Edwards Lifesciences Corporation, Irvine, CA (US)

(72) Inventors: Grigoriy Gorelik, West Hills, CA (US); Vladimir Zolotnik, West Hills, CA (US); James R. Cody, III, Tustin, CA (US); Ping-Yang Shih, Santa Ana, CA (US); Tiffany Diemtrinh Tran, Anaheim, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 665 days.

(21) Appl. No.: 16/258,143

(22) Filed: Jan. 25, 2019

(65) Prior Publication Data
US 2019/0223963 A1    Jul. 25, 2019

Related U.S. Application Data

(60) Provisional application No. 62/622,014, filed on Jan. 25, 2018.

(51) Int. Cl.
*A61B 34/30* (2016.01)
*A61B 34/00* (2016.01)
(Continued)

(52) U.S. Cl.
CPC ........ *A61B 34/30* (2016.02); *A61B 17/00234* (2013.01); *A61B 17/0469* (2013.01);
(Continued)

(58) Field of Classification Search
CPC .............. A61B 34/30; A61B 17/00234; A61B 17/0469; A61B 34/70; A61B 90/11;
(Continued)

(56) References Cited

U.S. PATENT DOCUMENTS 6,295,940 B1    10/2001  Shonteff
11,167,423 B1 *  11/2021  Hoffman .............. B25J 15/0266
(Continued)

FOREIGN PATENT DOCUMENTS

| GB | 2129283 A | 5/1984 |
|---|---|---|
| WO | 2015082713 A1 | 6/2015 |

OTHER PUBLICATIONS

Patent Cooperation Treaty, "International Search Report and Written Opinion of the International Searching Authority" re International Application No. PCT/US2019/015232 dated May 1, 2019, 13 pages.
(Continued)

*Primary Examiner* — Thomas McEvoy
(74) *Attorney, Agent, or Firm* — Edwards Lifesciences

(57) ABSTRACT

A semi-automatic precision positioning robot apparatus and method for use of the same to hold, position, orient and/or move a workpiece are provided. The positioning apparatus utilizes an actuator system of a given configuration to manipulate a workpiece holding unit with multiple degrees of freedom to achieve various positions and orientations. An associated tool may further be provided to interact with the workpiece in various positions and orientations. The positioning apparatus enables an operator to obtain high degrees of maneuverability while maintaining precision and consistency in the manufacture and production of various products and components.

18 Claims, 13 Drawing Sheets

(51) Int. Cl.
*A61B 90/11* (2016.01)
*A61B 17/00* (2006.01)
*A61B 17/04* (2006.01)
*A61F 2/24* (2006.01)
*B25J 9/00* (2006.01)

(52) U.S. Cl.
CPC .............. *A61B 34/70* (2016.02); *A61B 90/11* (2016.02); *A61F 2/2427* (2013.01); *B25J 9/0096* (2013.01); *A61B 2017/00243* (2013.01); *A61B 2017/00526* (2013.01); *A61B 2017/0496* (2013.01); *A61B 2034/305* (2016.02); *A61F 2/24* (2013.01)

(58) Field of Classification Search
CPC .. A61B 2017/00243; A61B 2017/0496; A61B 2034/305; A61F 2/2427
See application file for complete search history.

(56) References Cited

U.S. PATENT DOCUMENTS

| | | |
|---|---|---|
| 2005/0013841 A1 | 1/2005 | Phillips et al. |
| 2008/0035038 A1 | 2/2008 | Ekholm et al. |
| 2010/0257735 A1 | 10/2010 | Chambers et al. |
| 2014/0033959 A1 | 2/2014 | Evans et al. |
| 2016/0288317 A1* | 10/2016 | Gheorghe ................ B25J 9/003 |
| 2017/0252920 A1 | 9/2017 | Motomura et al. |

OTHER PUBLICATIONS

Patent Cooperation Treaty, International Preliminary Report on Patentability issued in PCT/US2019/015232, dated Aug. 6, 2020, pp. 1-10.

* cited by examiner

SEMI-AUTOMATIC PRECISION POSITIONING ROBOT APPARATUS AND METHOD

RELATED APPLICATIONS

This application claims the benefit of U.S. Provisional Application No. 62/622,014, filed Jan. 25, 2018, the contents of which are incorporated herein by reference in its entirety.

FIELD OF INVENTION

The present embodiments relate generally to positioning systems that are used to hold and position a workpiece. While the present embodiments may be used in a broad range of applications in various industries, a particular embodiment relates to an apparatus that assists in the assembly of components of a fabric-covered prosthetic heart valve, and associated methodology.

BACKGROUND

Manufacturing processes involving human participation often suffer from quality control problems due to human error. Manufacturing processes involving human participation also often cause operator stress and even injury. These quality control, stress, and/or injury problems are pronounced in manufacturing processes requiring sustained focus and manual dexterity due to fatigue. Consequently, there is often a desire to reduce human involvement and automate manufacturing processes. Automation of many manufacturing processes is not easy. For example, mechanical positioning systems used to hold and position a workpiece are utilized in various fields for a number of applications, such as manufacturing, machining, and assembly. Such positioning systems typically require a considerable degree of maneuverability and highly precise positioning of the workpiece in order to obtain the level of quality desired for each workpiece.

SUMMARY OF THE INVENTION

One aspect of the present disclosure relates to a semi-automatic precision positioning robot apparatus and method for use to hold, position, orient and/or move a workpiece. The positioning apparatus includes a support frame or casing, which can be an independent structure, allowing the positioning apparatus to be a self-contained unit, or the casing may be embedded into another structure or surface. In some embodiments, a vacuum may be integrated into the casing to help suction and contain any particulates or noxious fumes that are emitted during the manufacturing or work process.

Embodiments of the positioning apparatus utilize a plurality of linear actuators to position and orient the workpiece. The plurality of linear actuators may be attached to the support frame or casing in any suitable manner, including fixing the plurality of actuators between frame posts and/or to a frame base. The plurality of linear actuators includes a plurality of slide tracks and a plurality of slidable bases that move along the plurality of slide tracks. The plurality of slidable bases may have at least one movable platform receiving groove, which allows connecting portions of a movable platform to travel on a course defined by the groove. The plurality of linear actuators may be actuated to hold, position, orient, and move the workpiece by manipulating the position and orientation of a workpiece holding unit. The plurality of linear actuators can be actuated, alone or in conjunction with each other, to raise or lower the workpiece holding unit, as well as to move the workpiece holding unit side to side. Various embodiments may vary in the types and numbers of actuators used.

The positioning apparatus may include a gear system that allows for further manipulation of the position and orientation of the workpiece holding unit. The gear system includes a plurality of gear chains. A gear chain may include a rotary actuator coupled to the movable platform. The rotary actuator may rotate a gear shaft, which may, in embodiments, have a worm wheel on the end. As the gear shaft is rotated, the worm wheel spins, which in turn may drive a worm gear. Coupled to each worm gear may be a bevel gear, which rotates as the worm gear is driven. The gear system may include a workpiece holding unit bevel gear that couples with the bevel gear of individual ones of the plurality of gear chains. The plurality of gear chains can be driven such that the bevel gears rotate in the same direction, rotating the workpiece holding unit about an axis as the workpiece holding unit bevel gear, which is coupled to the bevel gears, orbits around the axis in a course determined by the rotation of the bevel gears. The plurality of gear chains can also be driven such that the bevel gears rotate in opposite directions (e.g., one clockwise and the other counter-clockwise), rotating the workpiece holding unit about an axis defined by a line that is perpendicular to the axis and that travels through the center of the workpiece holding unit bevel gear, as the workpiece holding unit bevel gear, which is coupled to the bevel gears, spins in place with respect to the axis. Various embodiments may vary in the types and numbers of components used, as well as their configuration, as needed. For example, in some embodiments, the gears may be bevel gears, planetary gears, or other similar types of gears. In some embodiments, the system may include (e.g., miniature) drive belts, (e.g., precision) chains, sprockets, and/or other components.

The positioning apparatus may include a tool, mounted in a location that allows the tool to interact with the workpiece. The tool includes a tool rotary actuator, which is configured to facilitate various possible angles of contact between the tool and the workpiece.

The positioning apparatus may establish a coordinate system, facilitating positioning and orientation of the workpiece and the tool according to defined coordinates.

For applications that require human supervision and/or other applications, the positioning apparatus may include a video camera for monitoring the work, which may also be configured for remote viewing by an off-site supervisor, for example, through an operatively coupled computer.

The various components of the positioning apparatus may be selectively controlled by an external controller.

The positioning apparatus may be used in a number of different applications, such as the manufacture of various mechanical and electronic products and components, manufacture and production of fine jewelry, and soldering, cutting, and assembly processes. Specific embodiments of the positioning apparatus may be fitted for the manufacture of medical devices, such as for example, including stitching materials onto prosthetic valves.

For embodiments of the positioning apparatus used to manufacture medical devices, including stitching materials onto prosthetic valves, the positioning apparatus may use a needle guide as the tool, including a needle guide rotary actuator, a guidance structure, and a stitching needle. A tensioning device incorporating a suture catch and release may also be provided to hold the thread (substantially) still and taut, or with the desired amount of tension, which can assist in creating proper stitches and avoiding entanglement of the thread. The tensioning device may be a magnetic assembly, for example, a spring assembly, and/or include other devices. In some embodiments, the tensioning device comprises a tensioning device base and a magnetic head. The operator may utilize the tensioning device by placing a section of thread behind the tensioning device (relative to the valve base structure), inserting the section of thread between the tensioning device base and magnetic head, and tautening the thread. The operator may release the tension on the thread whenever desired by pulling on the thread with enough force to allow the thread to move between the tensioning device base and magnetic head to the other side of the tensioning device. The magnetic strength of the magnetic head can be adjusted to determine the amount of force needed to allow the thread to move in such a manner, allowing the operator to obtain various levels of tension. The magnetic head can be kept in correct position (i.e., in a position where the magnetic head maintains a magnetic connection to an appropriate portion of the tensioning device base instead of being displaced to a location that renders the tensioning device inoperable) by any number of suitable means, including a displacement prevention lip on the tensioning device base or a displacement prevention chamber that allows the magnetic head sufficient range of movement for the thread to pass between the magnetic head and the tensioning device base but restricts the range of movement such that the magnetic head cannot fully exit the displacement prevention chamber. The structural arrangement of the tensioning device facilitates efficient and accurate tensioning required for the specific stitch or suture.

These and other objects, features, and characteristics of the apparatus or method disclosed herein, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure. As used in the specification and in the claims, the singular form of "a", "an", and "the" include plural referents unless the context clearly dictates otherwise.

DETAILED DESCRIPTION

Figure 1:
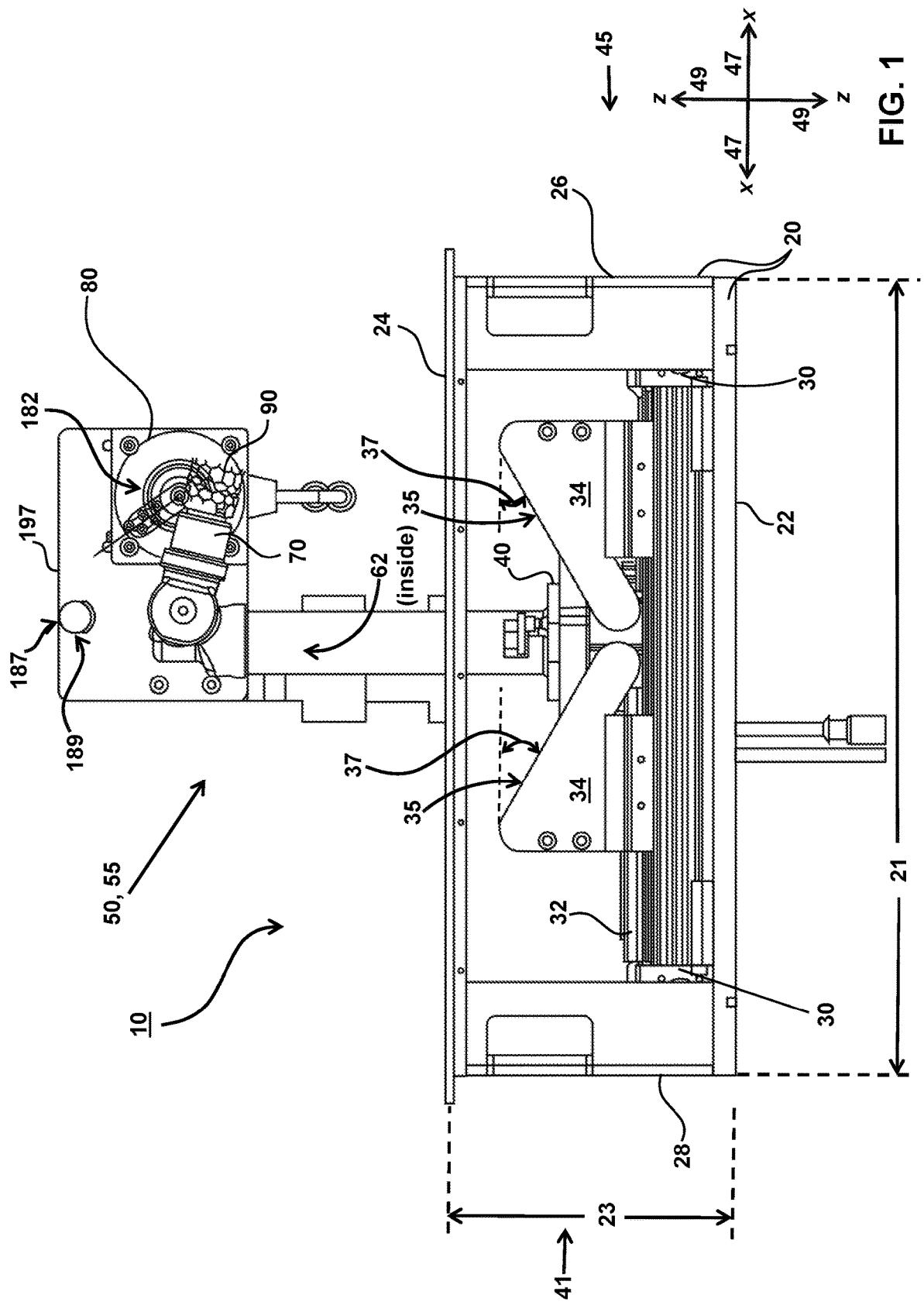
FIG. 1 is a side view of one embodiment of the robotic positioning apparatus.

The following description teaches the best mode of the invention through various embodiments. For the purpose of teaching inventive principles, some conventional aspects of the following embodiments may be simplified or omitted. Further, those skilled in the art will appreciate that the features described below can be substituted and/or combined in various ways to form multiple variations of the inventive embodiments. As a result, the invention is not limited to the specific examples and embodiments described below.

As a brief introduction, in order to achieve a large range of working positions, the positioning system may employ a number of actuators in a given configuration. The actuators may be individually or jointly actuated in order to position a component used to hold a workpiece. The actuators may use a gear system to transform the motion of the actuators in various ways. The number of actuators, the chosen configuration, and the presence of any additional components, such as the gear system, may affect the degree of maneuverability.

Complex actuator systems, however, often have relatively large aggregated (movement) error tolerances, leading to reduced positional precision, reduced stability, and/or other effects. Typical prior art positioning systems employing complex actuator systems in an effort to obtain higher degrees of maneuverability often suffer from such reduced precision and reduced stability. Current positioning systems also often lack a required level of rigidity. For example, smaller systems are often not rigid enough to maintain a desired (e.g., workpiece) position when force is applied to the workpiece (e.g., when a user is manipulating the workpiece as part of a manufacturing process). Larger systems may have the requisite rigidity, but the larger motors and added mass make these larger systems difficult or impossible to use in smaller scale applications (e.g., for manufacturing medical devices, etc.).

As such, typical prior art positioning systems are generally unsuitable for more sensitive applications or applications that require precise positioning on a small scale. This is more pronounced where the maneuverability and precise positioning must be repeatable, reliable, and consistent. One example of a relatively sensitive application involves the manufacture and assembly of medical devices. The acceptable range of error in manufacturing a medical device is narrow given the consequences of the presence of any flaws in such products. This is especially true for surgical implants and/or other products. As a result, the manufacture of surgical implants is often regulated by rigorous quality control standards and involves complex assembly procedures and considerations.

As one example, the manufacture of fabric-covered medical devices, including but not limited to, heart valves or Abdominal Aortic Aneurysm (AAA) Vascular Grafts, is known to be an intricate process requiring precision and consistency with a low acceptable range of error. Conventionally, the manufacture of cloth-covered medical devices like AAA devices is accomplished using manual labor, by hand-sewing (with needle and thread) the cloth and/or animal tissue onto a metal stent. The typical assembly procedure for a fabric-covered medical device occurs in two stages. During the first stage, intermittent stitches are placed to secure the fabric in its gross position around a support component, such as a stent. In the second stage, a closely-spaced line of stitches is applied to complete the seam, all while maintaining a certain degree of tension on the fabric. The procedure requires the needle and thread to pass through multiple layers of fabric, and sometimes biological tissue, with precision and consistency. This procedure is manually intensive for operators, and may induce high levels of stress and/or injury (e.g., carpel tunnel related injuries) in the operators. The hand sewing procedure is repetitive, and thus, operators frequently experience repetitive motion injuries (thus resulting in increased costs associated with treatment of such injuries for their employers). The fabric is typically tightly fitted around the support component and stitches are placed individually. The unusual shape of the medical device, and varying dimensions, contributes to the difficulty of assembly. Typical prior art positioning systems do not provide the precision and stability necessary to meaningfully assist in this and other assembly procedures.

There is a need for an improved positioning system that is suitable for force and dimensionally sensitive applications, including assisting with the assembly of heart valves and/or other medical devices in a manner that reduces time and effort required to manufacturing a device, and reduces stress and potential for injury in operators, while maintaining or enhancing quality and reliability of the manufacturing process and or the device.

FIG. 1 shows an exemplary positioning apparatus 10. Apparatus 10 is an improved positioning apparatus that is suitable for force and dimensionally sensitive applications, including assisting with the assembly of heart valves and/or other medical devices in a manner that reduces time and effort required to manufacturing a device, and reduces stress and potential for injury in operators, while maintain or enhancing quality and reliability of the manufacturing process and or the device. In apparatus 10, the inclusion and/or novel arrangement of the various components described herein facilitate precision movement and stability and also help reduce the stress and potential for injury in operators.

Apparatus 10 includes a support frame 20. Support frame 20 comprises a frame base 22, a frame cover 24, a first set of frame posts 26, a second set of frame posts 28, and/or other components. In some embodiments, support frame 20 may be an independent structure, allowing positioning apparatus 10 to be a self-contained unit. In some embodiments, support frame 20 may be embedded into another structure or surface, such as a tabletop, bench, or wall, or positioning apparatus 10 may be built directly into such structures and surfaces. In some embodiments, a vacuum (not shown in FIG. 1) may be integrated within frame 20 to facilitate suctioning and/or containment of particulates or noxious fumes, for example, that are emitted during a manufacturing process. Such a vacuum system may facilitate a clean and sanitary working environment, which is desirable in sensitive applications and those involving human operators. In some embodiments, frame 20 may surround and/or enclose other components of apparatus 10. In some embodiments, frame 20 may provide an anchor point and/or other attachment points for fixed or removable coupling of other components of apparatus 10.

In some embodiments, frame 20 may include brackets, nuts, bolts, screws, and/or other components configured to couple the various components of frame 20. Frame 20 may be formed from metal (e.g., aluminum, steel, etc.), polymers, ceramics, and/or other materials. For example, in some embodiments, base 22, cover 24, posts 26, posts 28, and/or other components of frame 20 may be formed from aluminum, steel, and/or other materials. As another example, individual components may have oxide layers, polymer and/or other coatings, and/or other features. In some embodiments, frame 20 may have a generally rectangular shape and/or other shapes. In some embodiments, frame 20 may have a length 21. In some embodiments, frame 20 may have a height 23. In some embodiments, a material, a shape, a size, and/or other characteristics of frame 20 and/or components of frame 20 may be configured to enhance a weight and/or a stability of frame 20.

Figure 2:
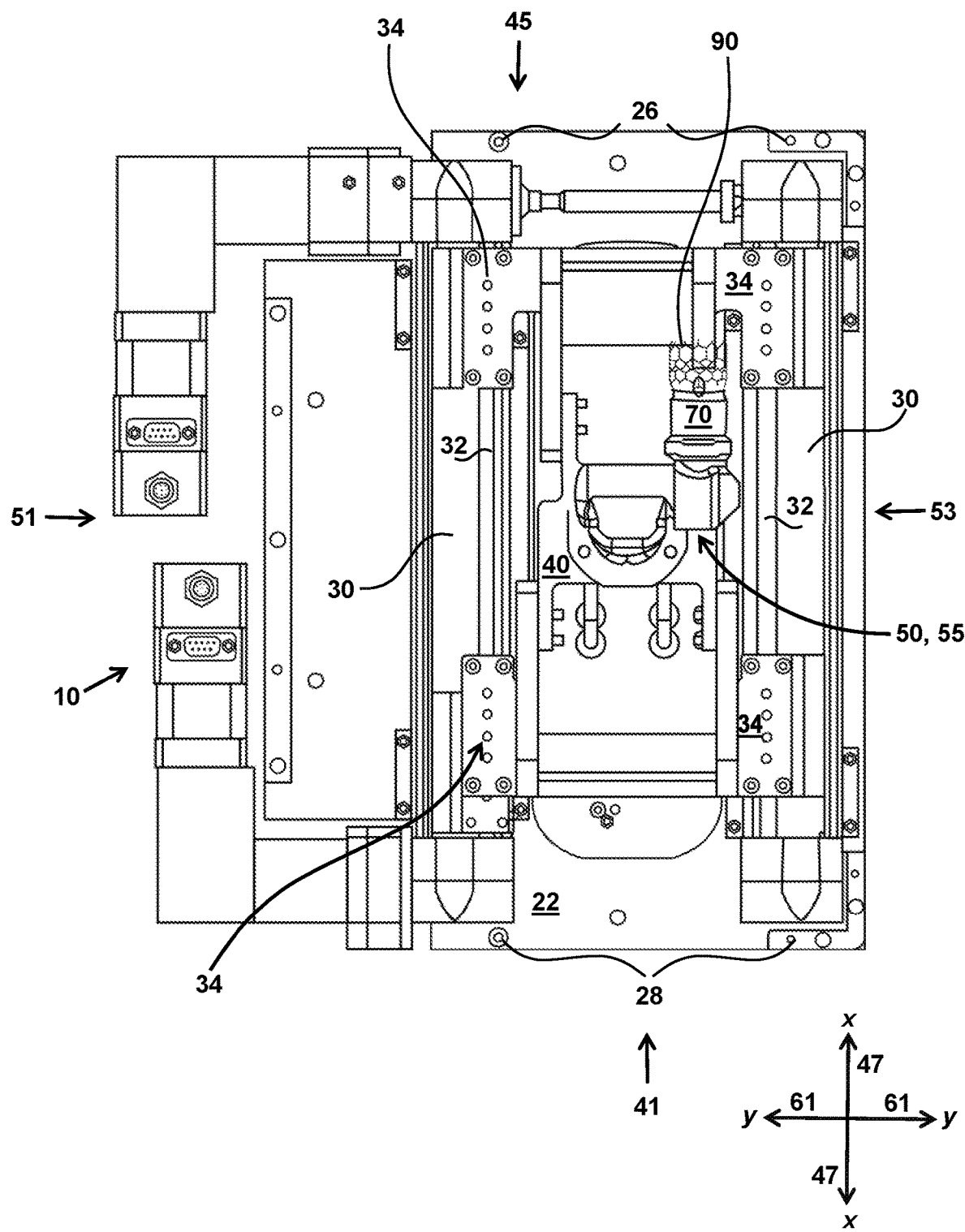
FIG. 2 is a top view of one embodiment of the robotic positioning apparatus with the cover of the support frame removed.

Fixedly attached to the support frame 20 is a plurality of linear actuators 30, as illustrated in FIG. 2. A linear actuator 30 may be and/or include a Toothed Belt Axis ECG-50-TB-KF linear actuator from Festo Corporation and/or other components, for example. The plurality of linear actuators 30 may be fixed between the first set of frame posts 26 and the second set of frame posts 28, attached to the frame base 22, and/or positioned in any other manner that secures the plurality of linear actuators 30 within the support frame 20. The plurality of linear actuators 30 includes a plurality of slide tracks 32 and a plurality of slidable bases 34 that move along the plurality of slide tracks 32. It should be understood that any suitable type of linear actuator may be utilized. The plurality of linear actuators 30 can be actuated by any means (pneumatically, electrically, hydraulically, by servo drive, etc.). In some embodiments, apparatus 10 includes a pair of slidable bases 34 with a first slidable base 39 located toward a first end 41 of frame 20, and a second slidable base 43 located toward a second end 45 of frame 20. In some embodiments, bases 39 and 43 are positioned on opposite sides of workpiece holding unit 70 along an x-axis 47 of apparatus 10 that extends from end 41 to end 45.

Figure 3:
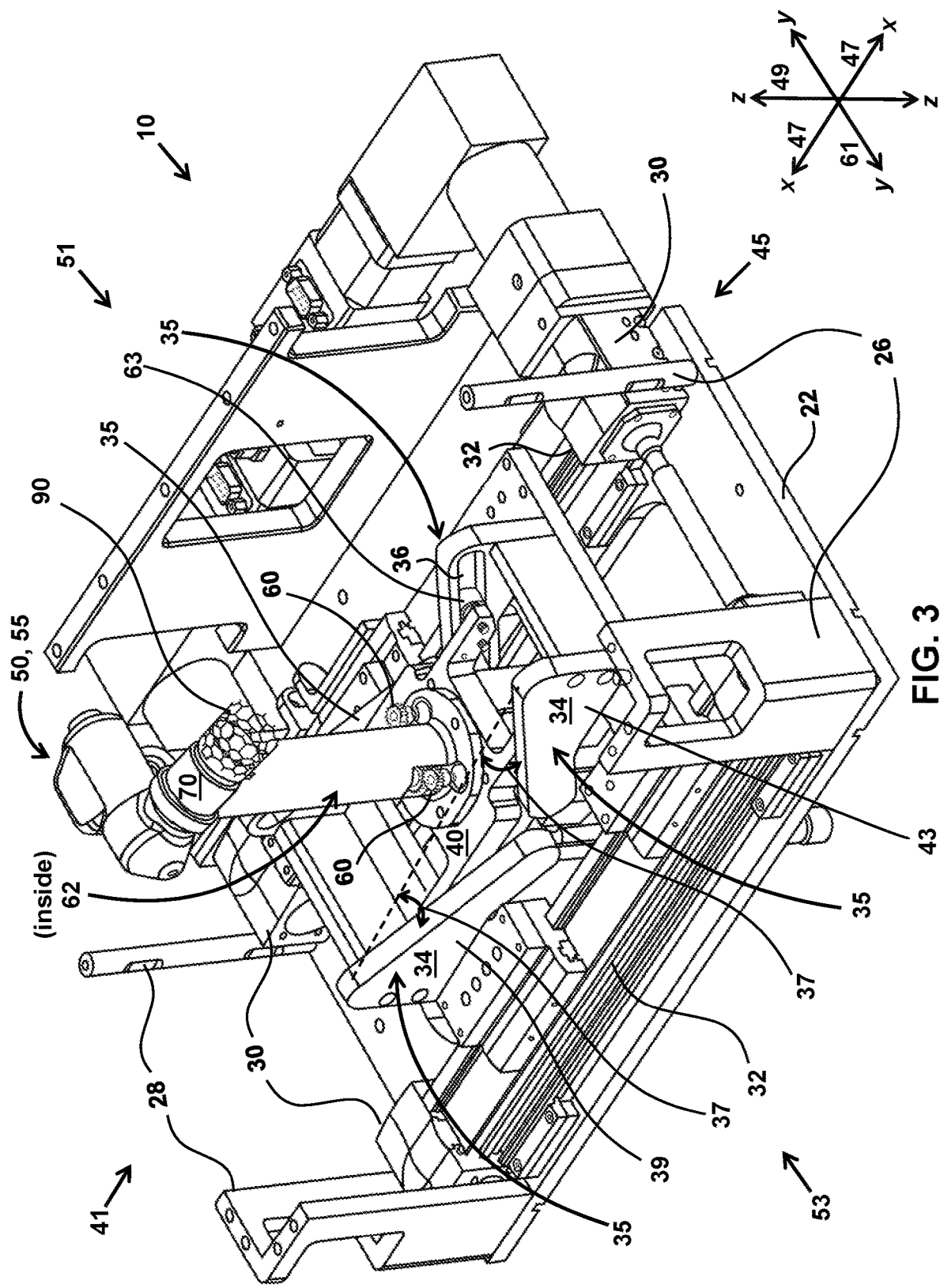
FIG. 3 is a perspective view of one embodiment of the robotic positioning apparatus with the cover of the support frame removed.

As seen in FIG. 3, the plurality of slidable bases 34 have at least one movable platform receiving groove 36, which allows connecting portions (e.g., wheels 63 and/or other connecting portions as shown in the example in FIG. 3) of the movable platform 40 to travel on a course defined by the at least one movable platform receiving groove 36. Grooves 36 may be formed in or by angled portions 35 of slidable bases 34. In some embodiments, an individual slidable base 34 includes two angled portions 35 formed on opposite sides of an individual base 34. For example, as shown in FIG. 3, a slidable base 34, includes an angled portion 35 located toward a side 51 of frame 20 and another angled portion 35 located toward an opposite side 53 of frame 20 (along a y-axis 61 of apparatus 10). In some embodiments, apparatus 10 comprises four grooves 36, with one groove 36 formed in each of four individual angled portions 35 of slidable bases 34. In some embodiments, grooves 36 extend along angled portions 35 from a location of an angled portion 35 located toward base plate 22 in a direction away from base plate 22 toward end 41 (base 39) or 45 (base 43) along x-axis 47, and along a z-axis 49. In some embodiments, angled portions 35 and/or grooves 36 may form an angle 37 relative to base plate 22.

The positioning apparatus 10 can be used to hold, position, orient, and/or move a workpiece 90 by manipulating the position and orientation of the workpiece holding unit 70. The plurality of linear actuators 30 can be actuated to raise or lower (in combination with grooves 36) the workpiece holding unit 70 (i.e., to translate the workpiece holding unit 70 along z-axis 49), generating one degree of freedom. The linear actuators 30 can also be actuated to move the workpiece holding unit 70 from side to side (i.e., to translate the workpiece holding unit 70 along x-axis 47) adding an additional degree of freedom, combining to two degrees of freedom.

For example, one embodiment of the positioning apparatus 10 can be set at what may be referred to as a neutral position, where the workpiece holding unit 70 is centered along the Z (49) and X (47) axes. The two slidable bases 34, each with two movable platform receiving grooves 36 can be used as described above. The movable platform receiving grooves 36 of the slidable base 34 that is closer to the first set of frame posts 26 (e.g., end 45) can be angled (e.g., as described above) to set a course that travels away from frame cover 24 (FIG. 1) toward the frame base 22 (e.g., along z-axis 49) as it travels away from the first set of frame posts 26 (end 45) toward the second set of frame posts 28 (e.g., along x-axis 47 toward end 41). The movable platform receiving grooves 36 of the slidable base 34 that is closer to the second set of frame posts 28 (e.g., end 41) can be angled to set a course that travels away from frame cover 24 toward the frame base 22 (e.g., along z-axis 49) as it travels away from the second set of frame posts 28 (end 41) toward the first set of frame posts 26 (e.g., along x-axis 47 toward end 45). In this configuration, illustrated in FIG. 3, the workpiece holding unit 70 can be raised along z-axis 49 by actuating the plurality of linear actuators 30 toward each other, such that the movable platform 40 travels along the course set by the movable platform receiving grooves 36 toward the frame cover 24. The workpiece holding unit 70 can be lowered along z-axis 49 by actuating the plurality of linear actuators 30 away from each other, such that the movable platform 40 travels along the course set by the movable platform receiving grooves 36 toward the frame base 22. In some embodiments, a typical translation along z-axis 49 may be on the order of millimeters, centimeters, or more. The workpiece holding unit 70 can be translated along x-axis 47 by actuating the plurality of linear actuators 30 in the same direction, such that the movable platform 40 does not travel along the course set by the movable platform receiving grooves 36.

It is to be understood that different embodiments may vary in the types, number, and/or the orientation of the components (e.g., actuators, slide tracks, slidable bases, moveable platform receiving grooves) used. Although the exemplary positioning apparatus 10 shown in FIG. 3 uses two linear actuators, two slide tracks, two slidable bases, and the given groove orientation, it should be understood that this configuration is illustrated for exemplary purposes only and any suitable type, number, and/or orientation of these components may be used.

Figure 4:
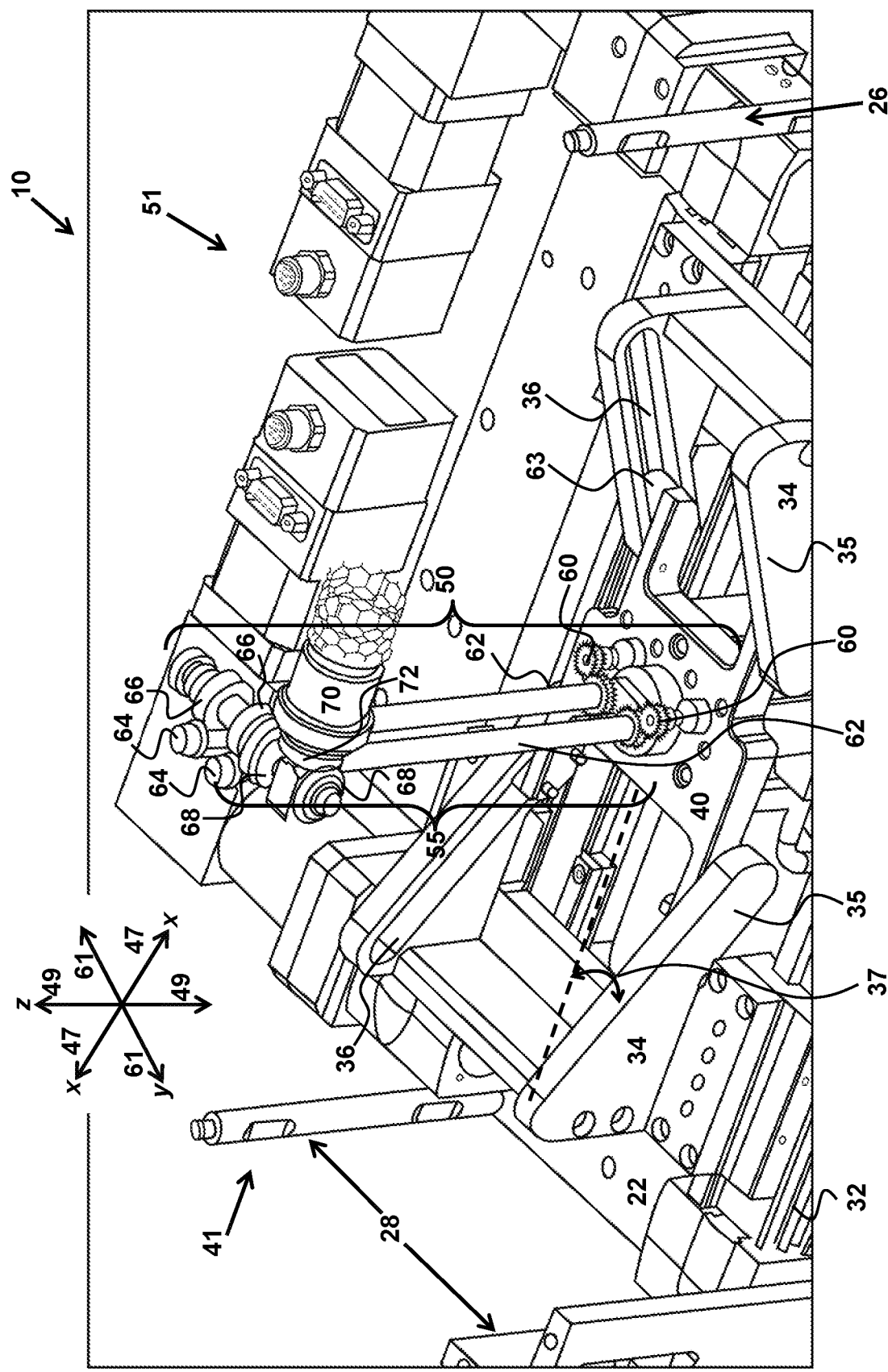
FIG. 4 is a partial perspective view of one embodiment of the robotic positioning apparatus with the cover of the support frame removed and the gear system exposed.
Figure 5:
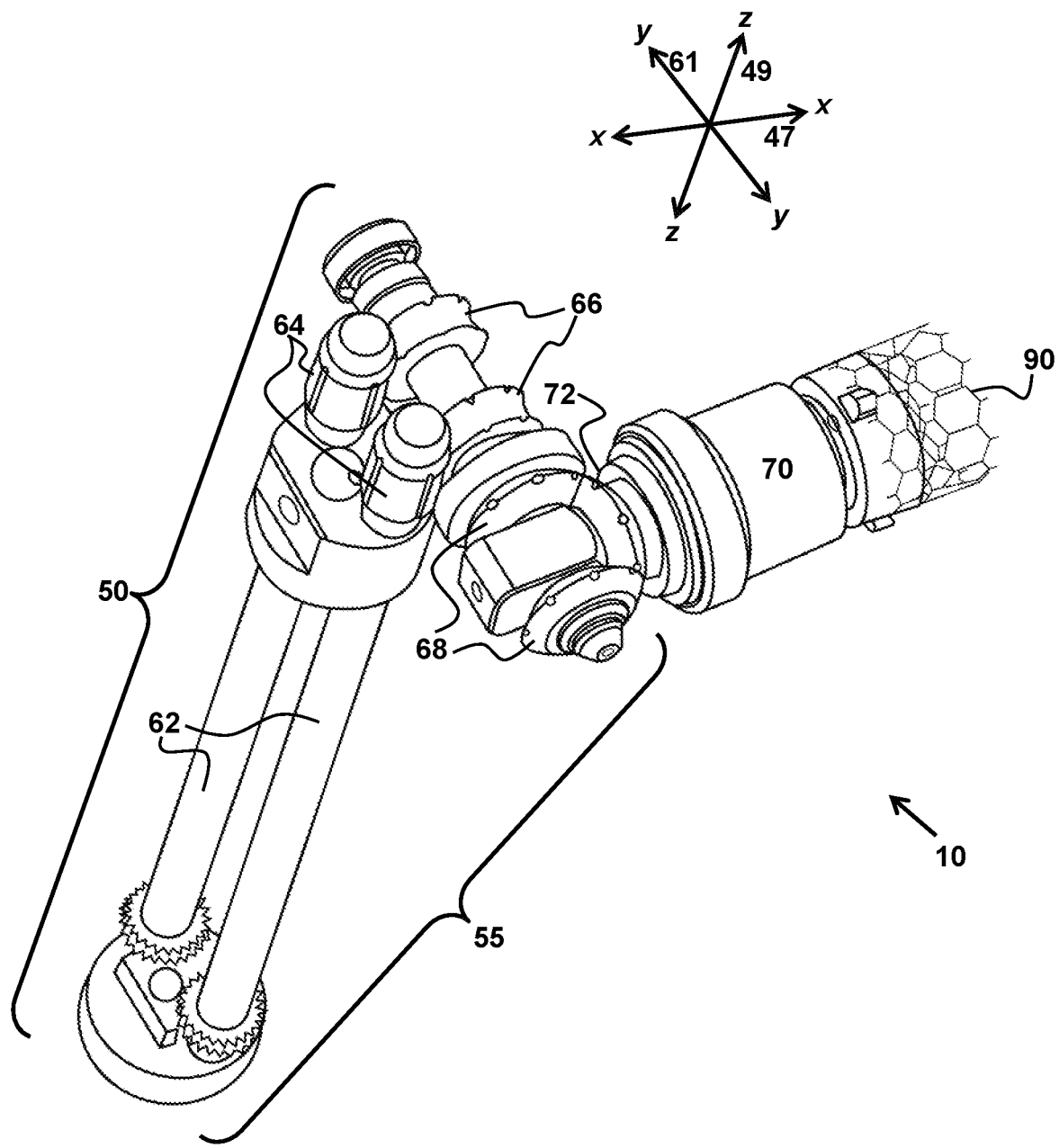
FIG. 5 is a perspective view of one embodiment of the gear system and workpiece holding unit of the robotic positioning apparatus.

FIGS. 4 and 5 illustrate a gear system 50 configured to facilitate further manipulation of the position and orientation of the workpiece holding unit 70. The gear system 50 includes a plurality of gear chains 55. A (e.g., each) gear chain 55 may include a rotary actuator 60 that is attached to the movable platform 40. Rotary actuator 60 may be and/or include Rotary Drive ERMO-12-ST-E from Festo Corporation, for example, and/or other components. Rotary actuator 60 may be and/or include one more of a metal gear with a 20 degree pressure angle round bore (48 pitch, 18 teeth—McMaster Carr part number 7880K190), for example, and/or other components. It should be understood that any suitable type of rotary actuator may be utilized. The rotary actuator 60 may then rotate (drive) one end of a gear shaft 62, which may have a worm wheel 64 located on the opposite end. A gear shaft 62 may be and/or include a linear motion shaft, 1055 carbon steel, 8 mm diameter, 200 mm length (McMaster Carr part number 6112K44), for example, and/or other components. A worm wheel 64 may be and/or include a W Worm, Kyouiku Gear, W80SUR1+B from Misumi USA, for example, and/or other components. An individual gear shaft 62 may include a gear 71 configured to engage a rotary actuator 60. Gear(s) 71 may be located at or near an end of a gear shaft 62 toward moveable platform 40. A gear 71 may be and/or include a metal gear with a 20 degree pressure angle round bore (48 pitch, 24 teeth—McMaster Carr part number 7880K210), for example, and/or other components. An individual gear shaft 62 may be positioned along z-axis 49 and extend from moveable platform 40 in a direction along z-axis 49 away from base plate 22. As a gear shaft 62 is rotated, the worm wheel 64 spins, which in turn may drive a worm gear 66. A worm gear 66 may be and/or include Worm Wheels, G Series, Kyouiku Gear, G80A20+R1 from Misumi USA, for example, and/or other components. Coupled to individual worm gears 66 may be bevel gears 68 (with an individual bevel gear 68 engaged with an individual worm gear 66), which rotate as the worm gears 66 are driven. A bevel gear 68 may be and/or include a Ground Tooth Spiral Miter SMSG1-20RJ6 from Misumi USA, for example, and/or other components. It should be understood that the gear chains 55 may be any combination and configuration of components and gears that ultimately drives the bevel gear 68 of the gear chain 55. The gear system 50 may further include a workpiece holding unit bevel gear 72 that couples with the bevel gear 68 of each of the plurality of gear chains 55. A bevel gear 72 may be and/or include a Ground Tooth Spiral Miter SMSG1-20LJ6 from Misumi USA, for example, and/or other components.

As shown in FIG. 5, in some embodiments, worm wheel(s) 64 may be positioned along z-axis 49, substantially parallel to gear shaft(s) 62. Worm gear(s) 66, bevel gears 68, and/or other components may be positioned along y-axis 61 substantially perpendicular to gear shaft(s) 62. Bevel gear 72, workpiece holding unit 70, workpiece 90, and/or other components may be positioned along x-axis 47, substantially perpendicular to both gear shaft(s) 62 and bevel gear 68 and worm gears 66. It should be noted that these components are configured to rotate in various directions and the arrangement and position shown in FIG. 5 is an example only.

Figure 6:
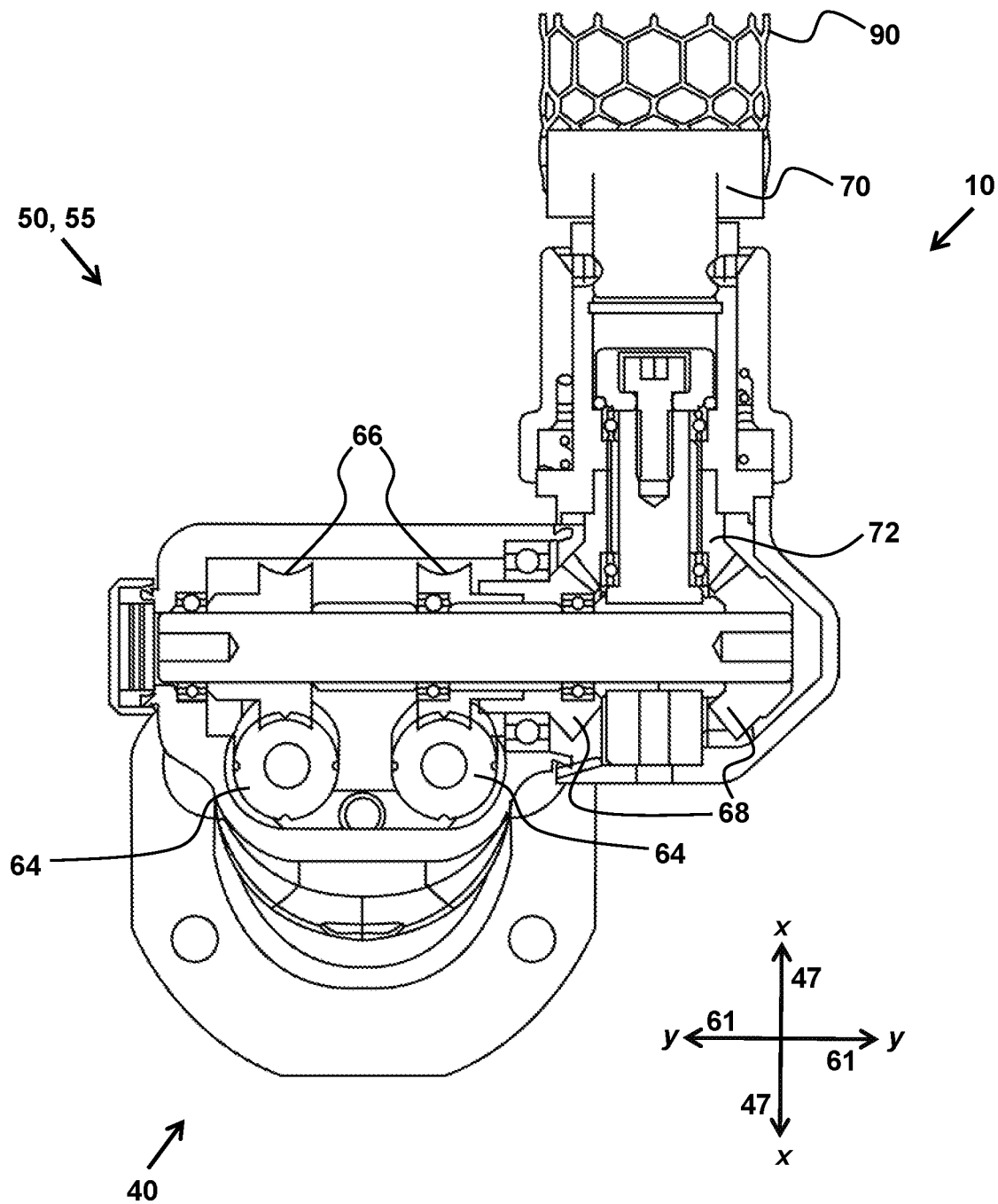
FIG. 6 is a top cross-sectional view of one embodiment of the gear system and workpiece holding unit of the robotic positioning apparatus.

FIG. 6 illustrates one possible arrangement of the worm wheel(s) 64, worm gear 66, and bevel gear 68 components of the plurality of gear chains 55 and the coupled workpiece holding unit bevel gear 72. By driving the plurality of gear chains 55 such that the bevel gears 68 rotate in the same direction, rotation of the workpiece holding unit 70 about an x-axis 47 (in this example) is achieved, as the workpiece holding unit bevel gear 72, which is coupled to the bevel gears 68, orbits around the x-axis in a course determined by the rotation of the bevel gears 68. This adds an additional degree of freedom, to a total of three degrees of freedom. By driving the plurality of gear chains 55 such that the bevel gears 68 rotate in opposite directions (e.g., one clockwise and the other counter-clockwise), rotation of the workpiece holding unit 70 about an axis defined by a line that is perpendicular to the x-axis and that travels through the center of the workpiece holding unit bevel gear 72 is achieved, as the workpiece holding unit bevel gear 72, which is coupled to the bevel gears 68, spins in place with respect to the x-axis. This adds yet another degree of freedom, to a total of four degrees of freedom.

It is to be understood that alternative embodiments may vary in the types and numbers of gears used, as well as their configuration, as needed. For example, in alternative embodiments, the gears may be bevel gears, planetary gears, or other similar types of gears. The plurality of gear chains and its rotary actuators may be selectively actuated by an external controller. The controller may be any suitable type of controller, such as, for one example, a programmable logic controller. In some embodiments, the gears may be replaced by one or more (e.g., miniature) drive belts, (e.g., precision) chains, sprockets, and/or other components. Using these alternatives, or a combination of gears and these alternatives, may provide more optimal use of power and resulting torque in the system.

Returning to FIG. 1, various embodiments of the positioning apparatus 10 may be configured to perform different applications. Any industry requiring precise and consistent manufacturing processes, and/or reduced stress and potential for injury in operators, may employ the positioning apparatus 10 to provide high degrees of maneuverability and precise contact points. In the health industry, for example, the positioning apparatus 10 may be used to manufacture and produce medical devices (e.g., as described herein). In various fields, the positioning apparatus 10 may be used to manufacture and produce mechanical or electronic products and components. In the fashion industry, the positioning apparatus 10 may be used to manufacture and produce fine jewelry. The positioning apparatus 10 may be used in processes requiring precise soldering, cutting, assembly, painting, and the like. The foregoing applications are not inclusive and embodiments of the positioning apparatus 10 may be used in many other applications not expressly described. Embodiments of the present apparatus may be of varying size depending on the scale required by the particular application.

Figure 7:
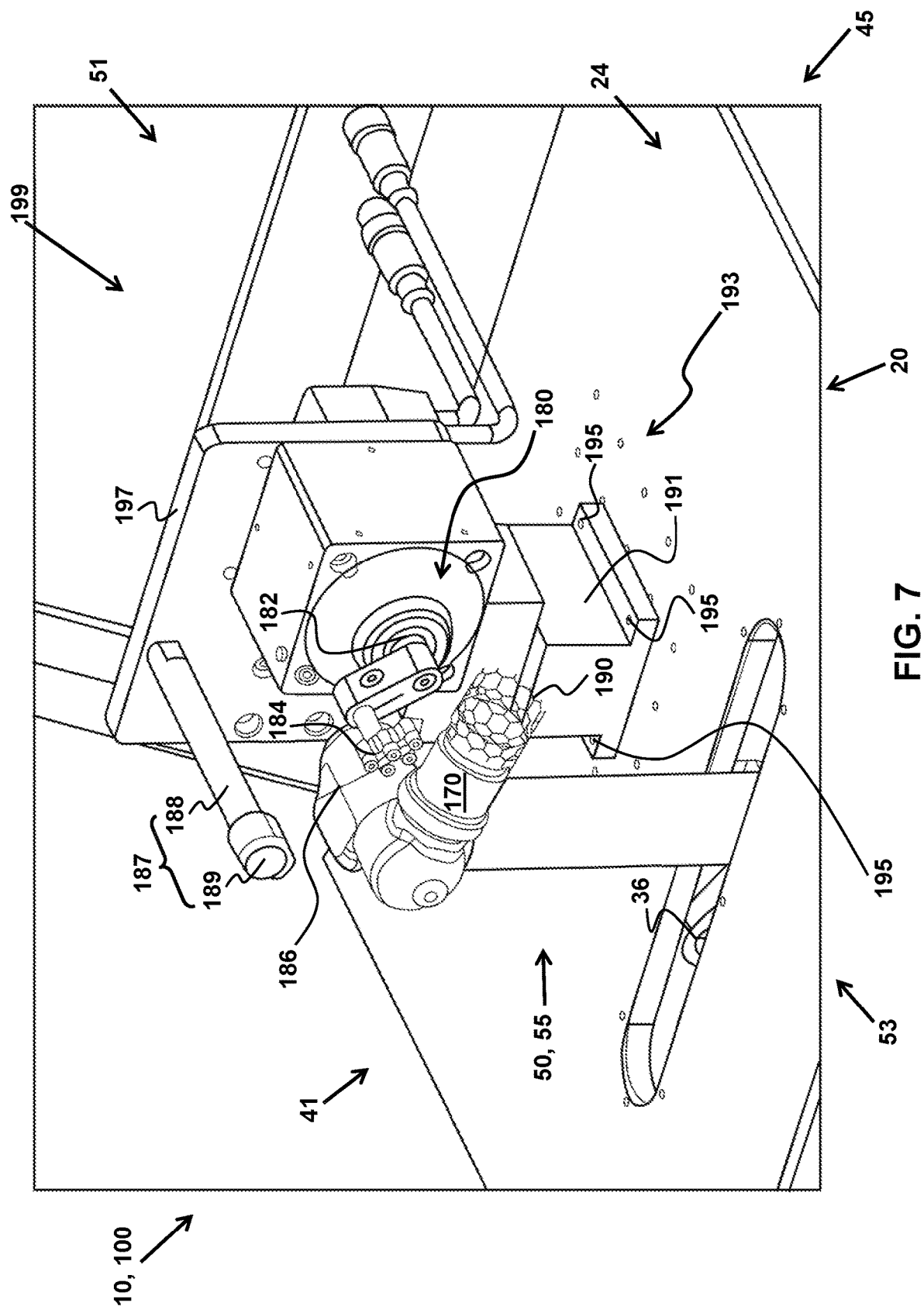
FIG. 7 is a close-up perspective view of a specific application of one embodiment of the robotic positioning apparatus.
Figure 8:
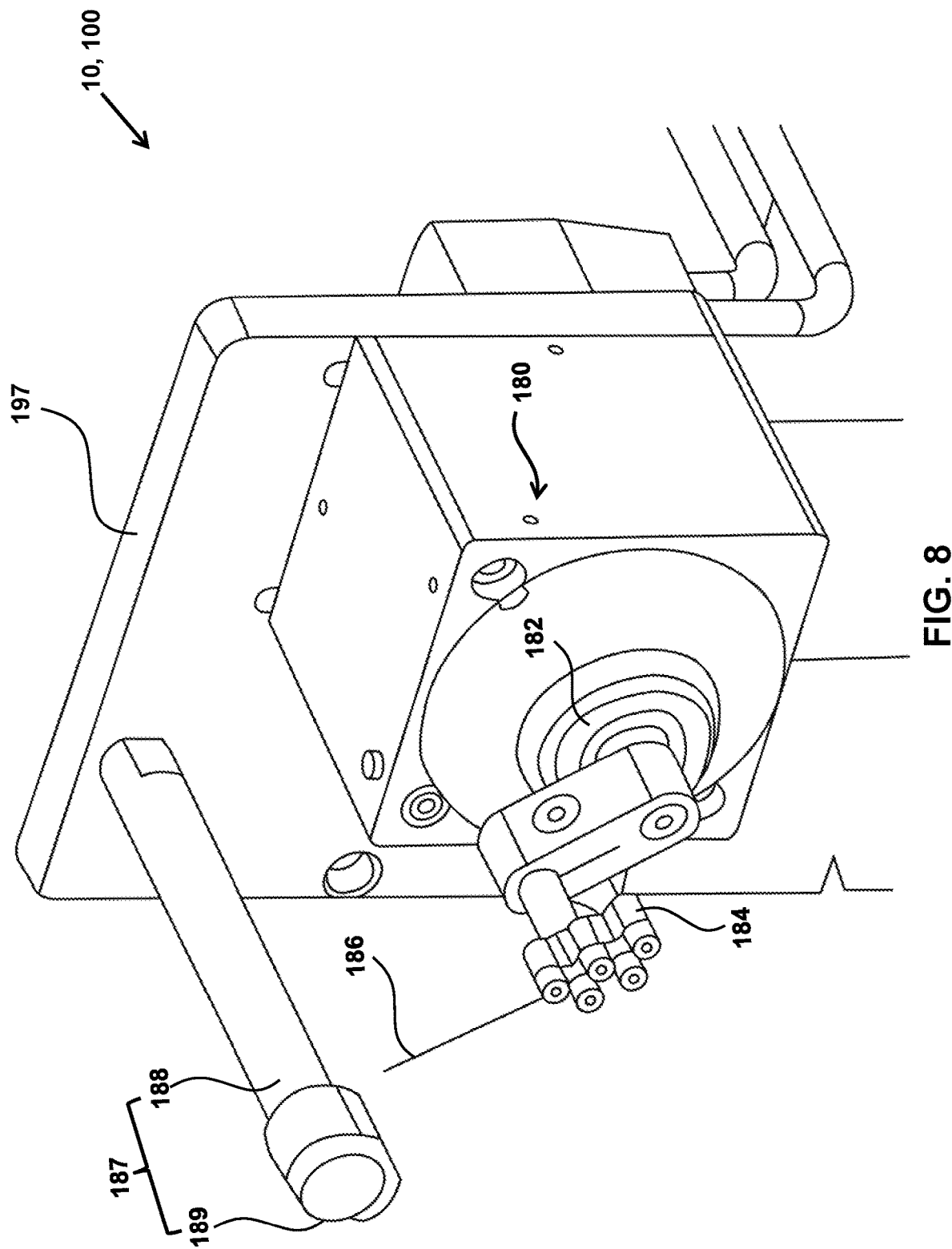
FIG. 8 is a close-up perspective view of the tool portion of a specific application of one embodiment of the robotic positioning apparatus.

The positioning apparatus 10 may include a tool 80, mounted in a location that allows the tool 80 to interact with the workpiece 90 in the various working positions and orientations achieved. Apparatus 10 includes a tool rotary actuator 182. It should be understood that any suitable type of rotary actuator may be utilized. The tool rotary actuator 182 can be actuated to rotate the tool 80 about y-axis 61 (FIG. 2, 3), resulting in various possible angles of contact between the tool 80 and the workpiece 90. Although this does not generate an additional degree of freedom of movement between the workpiece 90 and the tool 80, rotating the tool 80 may allow for angles of contact unobtainable by solely tilting, rotating, or otherwise moving the workpiece holding unit 70. The tool 80 may include additional components as desired for the specific application. For the specific application of manufacturing prosthetic heart valves, for example, the tool may be a needle guide that positions and orients the needle to the correct point and angle of entry for the desired stitch as shown in FIGS. 7 and 8, which will be discussed in further detail below.

The positioning apparatus 10 and its various actuators may be selectively actuated by an external controller and/or other components. The controller may be any suitable type of controller, such as, for one example, a programmable logic controller. The positioning apparatus 10 may comprise a coordinate system, facilitating positioning and orientation of the workpiece 90 and the tool 80 according to defined coordinates.

It is to be understood that various embodiments of the invention may vary in the orientation (e.g., horizontal, vertical, etc.) of the positioning apparatus and its various components (e.g., the linear actuators, the gear system, the workpiece holding unit, the workpiece, the tool) and that any suitable orientation may be used. For example, one embodiment may achieve a horizontal orientation with components installed horizontally into a reoriented outer casing or directly into a wall or other structure. The orientation of the X, Y, and Z axes referenced herein may be adjusted as desired and necessary.

For applications that require human supervision, the positioning apparatus 10 may include a video camera (not shown in FIG. 1) for monitoring the work. The video camera may be any suitable type of video camera and may provide enhanced visibility for the operator. The camera may also be configured to provide remote viewing by an off-site supervisor, for example, through a coupled computer via either a wired or wireless connection.

Figure 9:
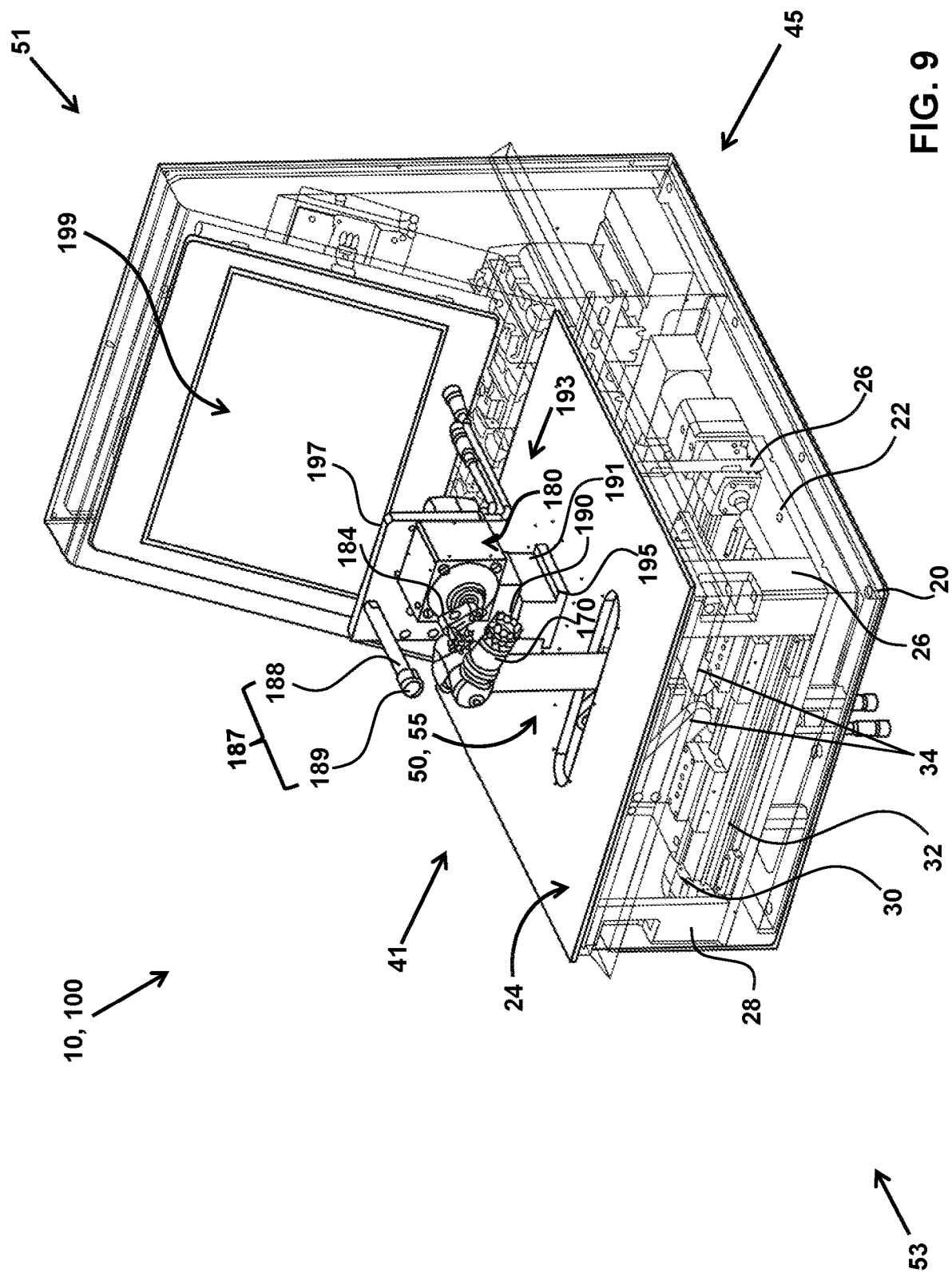
FIG. 9 is a perspective view of a specific application of one embodiment of the robotic positioning apparatus in one possible installation context.

In some embodiments, as described herein, the positioning apparatus 10 may be used to manufacture medical devices. In some embodiments, as shown in FIGS. 7-9, apparatus 10 may be and/or be included in a robotic positioning apparatus 100. During the manufacture of medical devices, for example, apparatus 10 and/or 100 may facilitate a semi-automatic method of stitching materials onto a prosthetic heart valve, and/or other medical devices. It is to be understood that the assembly of a fabric-covered prosthetic heart valve is an example of an application of the present apparatus, but the present apparatus is not to be limited to this example. The present apparatus may be used to attach any desired material to a prosthetic heart valve and can further be used for applications beyond prosthetic heart valve assembly.

In this example (where numerals in FIG. 7-9 (e.g., 1xx) correspond to like numerals in FIG. 1-6 (e.g., xx)), apparatus 10 (FIG. 1-6) and/or apparatus 100 (FIG. 7-9) may be configured such that an operator may begin manufacturing a prosthetic heart valve using apparatus 100 by attaching a valve base structure or scaffolding 190 to the valve holding unit 170 of the robotic positioning apparatus 100 and holding a tubular biocompatible fabric around the valve base structure 190, applying tension to the fabric as necessary to ensure that the stitches are properly made. The robotic positioning apparatus 100 may establish a coordinate system. The robotic positioning apparatus 100 may place the valve base structure 190 in the proper position and orientation according to the coordinate system, as well as position and orient a needle guide 180 (e.g., an example of a tool 80 shown in FIG. 1) such that a stitching needle 186 is aligned to an entry point for penetration according to the coordinate system. The needle guide 180 may also be oriented to a specific angle of contact relative to the valve base structure 190 to provide precise positioning and orientation for a desired stitch.

This positioning process is performed by apparatus 100 by selectively actuating the various actuators of the robotic positioning apparatus 100 (e.g., as part of apparatus 10 shown in FIG. 1-6). The robotic positioning apparatus 100 and its various actuators may be selectively actuated by an external controller and/or other components. The controller may be any suitable type of controller, such as, for one example, a programmable logic controller. The controller may selectively actuate the various actuators in response to various inputs by the operator. The controller may further be programmed to automatically place the valve base structure 190 in a number of predetermined positions and orientations or to follow a template defining a standardized stitching position order. Such a template may be created by programming the controller to locate a progressive series of discreet entry points and angles of contact.

Once the positioning process is complete, apparatus 100 is configured such that an operator may pull (push, and/or otherwise move) a stitching needle 186 through a needle guide 180 to a defined penetration point. The needle guide 180 is configured to reduce stress on an operator at least because needle guide 180 is configured such that an operator need only move stitching needle 186 in an axial direction, and not in lateral directions. As the operator does so, apparatus 100 is configured such that the stitching needle 186 releases the needle guide 180, allowing the operator to tension the stitch. The needle guide 180 may be configured to provide tensioning to the suture as needed during a stitch. After a stitch is complete, apparatus 100 is configured such that the operator may return the stitching needle 186 to the needle guide 180 and the robotic positioning apparatus 100 may proceed to the next stitch position to prepare for the next stitch. The needle guide 180 may continue to provide tension to the suture as necessary. Once the repositioning process is complete, the operator may complete the next stitch, and the process is repeated as needed until the stitching process is complete.

Needle guide 180 is configured to ensure needle penetration in a prescribed location. Needle guide 180 is configured to reduce operator fatigue during a stitching process because, using needle guide 180, an operator need only provide a linear or axial push to needle 186 to complete a stitch. An operator need not grasp and squeeze needle 186, for example, or manually determine angular or lateral movement. Needle guide 180 includes rollers configured to reduce friction and/or drag and, together with tensioning device 187 (described below), facilitates accurate stitch placement and thread tension. Needle guide 180 is configured such that needle 186 is not permanently attached to a moving head (e.g., such as a sewing machine), or used only manually. Needle guide 180 and needle 186 are configured such that needle 186 may repeatedly pass completely through a manufacturing (e.g., heart valve) assembly and be retrieved for a next stitch. By way of a contrasting example, a sewing machine is not configured in this way unless a bobbin apparatus is incorporated (which would not be feasible in this heart valve and other examples).

The needle guide 180 has a needle guide rotary actuator 182. It is understood that any suitable type of rotary actuator may be utilized. The needle guide rotary actuator 182 can be actuated to rotate the needle guide 180 and the stitching needle 186 about the y-axis 61, resulting in various possible angles of contact between the stitching needle 186 and the valve base structure 190. The needle guide 180 includes a guidance structure 184 to direct the stitching needle 186. The guidance structure 184 may be a rail, a track, guide rollers, guide wheels, a tube, or any other suitable mechanism. The guidance structure 184 may secure the stitching needle 186 until use by the operator through friction, a lock, or any other suitable mechanism.

A tensioning device 187 incorporating a suture catch and release mechanism may be provided to hold a thread substantially still and taut, or with a desired amount of tension depending on the application, which may assist in creating stitches and avoiding entanglement of the thread, among other advantages. The tensioning device 187 may be, for example, a magnetic assembly, a spring assembly, and/or other assemblies. In some embodiments, the tensioning device 187 comprises a tensioning device base 188 and a magnetic head 189. Base 188 and head 189 may be configured such that the tensioning device 187 is used by placing a section of thread behind the tensioning device 187 (relative to the valve base structure 190), inserting the section of thread between the tensioning device base 188 and magnetic head 189, and tautening the thread. The thread may be tautened in any suitable manner, including manually, such as pulling on the thread directly, by winding a spool or the source of the thread, and by moving the stitching needle 186, including by using the needle guide 180, needle guide rotary actuator 182, and guidance structure 184. The operator may release the tension on the thread whenever desired by pulling on the thread with enough force to allow the thread to move between the tensioning device base 188 and magnetic head 189 to the other side of the tensioning device 187. The magnetic strength of magnetic head 189 can be adjusted to determine the amount of force needed to allow the thread to move in such a manner, allowing the operator to obtain various levels of tension. The magnetic head 189 can be kept in correct position (i.e., in a position where the magnetic head 189 maintains a magnetic connection to an appropriate portion of the tensioning device base 188 instead of being displaced to a location that renders the tensioning device 187 inoperable) by any number of suitable means, including a displacement prevention lip on the tensioning device base 188 or a displacement prevention chamber that allows the magnetic head 189 sufficient range of movement for the thread to pass between the magnetic head 189 and the tensioning device base 188 but restricts the range of movement such that the magnetic head 189 cannot fully exit the displacement prevention chamber. The structural arrangement of the tensioning device 187 facilitates efficient and accurate tensioning required for the specific stitch or suture.

In some embodiments, the tensioning device 187 may be any other device configured to control tensioning during sewing (e.g., compared to prior devices which require an operator to manually control tensioning). In some embodiments, as described above, the tensioning device 187 may be a spring assembly.

In some embodiments, needle guide 180 and tensioning device 187 are coupled to frame 20 on frame cover 24 via a block 191 configured to support needle guide 180 and tensioning device 180. For example, frame cover 24 and block 191 may include corresponding through holes 193 (e.g., which form a hole pattern) and 195. Bolts, screws, nuts, and/or other coupling devices may be used in conjunction with holes 193 and 195 to couple block 191 to frame cover 24. In some embodiments, a plate 197 may be coupled to block 191 and components of needle guide 180 and/or tensioning device 187 may be coupled to plate 197. Plate 197 and block 191 may be positioned on a side of valve base structure 190 (or another workpiece 90—FIG. 1) toward side 51 of apparatus 100 (but this is not intended to be limiting). In some embodiments, components of needle guide 180 (e.g., rotary actuator 182, guidance structure 184) and/or tensioning device 187 (e.g., tensioning device base 188, magnetic head 189, etc.) may extend away from plate 197 toward valve base structure 190 (e.g., or another workpiece 90).

In some embodiments, for example, tensioning device base 188 may extend away from plate 197 and magnetic head 189 may be located at an end of tensioning device base 188 at or near valve base structure 190. In some embodiments, the tensioning device 187 comprises a suture tensioning arm (base) 188 that has a magnetic end (magnetic head 189) which may or may not be electrically energized. The electrically energized portion may allow for the option of using an electrical magnet, which may allow the user to adjust the magnitude of magnetic force whenever a change in suture tension is desired. A permanent magnet may also be used. A metal disc may be magnetically attached or attachable to the magnetic end and configured to allow for the suture to catch with an adjustable specified tension.

Figure 10:
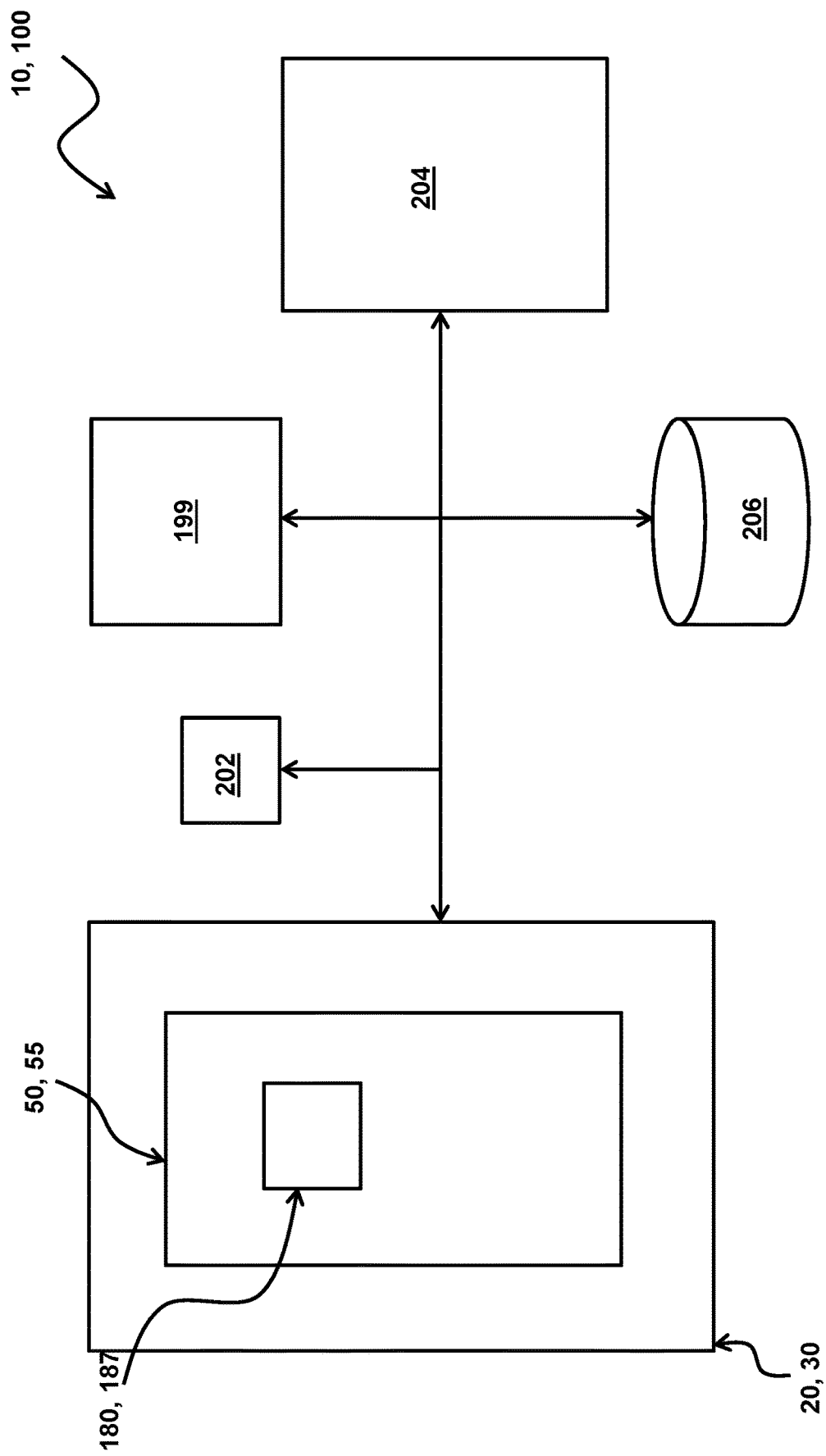
FIG. 10 is a schematic illustration of the present robotic positioning apparatus.

FIG. 10 is a schematic illustration of apparatus 10, 100. As shown in FIG. 10, apparatus 10, 100 may include a video camera 202 for monitoring the work (not shown in FIG. 7-9). The video camera 202 may be any suitable type of video camera. As each stitch may be inspected, the camera 202 may also function as a magnifier and provide enhanced visibility for the operator. If any stitch should be unsatisfactory, the operator may undo the stitch and program or position the robotic positioning apparatus 10, 100 to redo the unsatisfactory stitch before proceeding. The camera 202 may also be configured to provide remote viewing by an off-site supervisor, for example, through a coupled computer.

In some embodiments, as shown in FIG. 10 (and FIG. 9), apparatus 10, 100 may include a user interface 199. User interface 199 may be configured to provide an interface between apparatus 10, 100 and an operator (e.g., a technician, etc.) through which the operator may provide information to and receive information from apparatus 10, 100. This enables data, cues, results, and/or instructions and any other communicable items, collectively referred to as "information," to be communicated between the operator and apparatus 10, 100. Examples of interface devices suitable for inclusion in user interface 199 include a touch screen, a keypad, buttons, switches, a keyboard, knobs, levers, a display, speakers, a microphone, an indicator light, an audible alarm, a printer, and/or other interface devices. In some embodiments, user interface 199 includes a plurality of separate interfaces. In some embodiments, user interface 199 includes at least one interface that is provided integrally with frame 20. It is to be understood that other communication techniques, either hard-wired or wireless, are also contemplated by the present disclosure as user interface 199. For example, the present disclosure contemplates that user interface 199 may be integrated with a removable storage interface. In this example, information may be loaded into apparatus 10, 100 from removable storage (e.g., a smart card, a flash drive, a removable disk) that enables the operator to customize the implementation of apparatus 10, 100. Other exemplary input devices and techniques adapted for use as user interface 199 include, but are not limited to, an RS-232 port, RF link, an IR link, modem (telephone, cable or other). In short, any technique for communicating information with apparatus 10, 100 is contemplated by the present disclosure as user interface 199. By way of a non-limiting example, user interface 199 may be configured to display control fields, spatial information, video information, manufacturing instructions, quality control information, and/or other information.

In some embodiments, apparatus 10, 100 may include one or more processors 204, electronic storage 206, and/or other components. The one or more processors 204 may be configured to provide information-processing capabilities in apparatus 10, 100. As such, a processor 204 may comprise one or more of a digital processor, an analog processor, a digital circuit designed to process information, an analog circuit designed to process information, a state machine, and/or other mechanisms for electronically processing information. A processor 204 may be a single entity, or a processor 204 may comprise a plurality of processing units. These processing units may be physically located within the same device (e.g., apparatus 10, 100), or a processor 204 may represent processing functionality of a plurality of devices operating in coordination (e.g., a processor included in a remote server, etc.). The one or more processors 204, may run one or more electronic applications having graphical user interfaces configured to facilitate operator interaction with apparatus 10, 100, control the actuators, gears, and/or other mechanisms described herein, and/or perform other operations.

The electronic storage 206 may include electronic storage media that electronically stores information. The electronic storage media may include one or both of system storage that is provided integrally (i.e., substantially non-removable) with apparatus 10, 100 and/or removable storage that is removably connectable to apparatus 10, 100 via, for example, a port (e.g., a USB port, a firewire port) or a drive (e.g., a disk drive). The electronic storage 206 may include one or more of optically readable storage media (e.g., optical disks), magnetically readable storage media (e.g., magnetic tape, magnetic hard drive, floppy drive), electrical charge-based storage media (e.g., EEPROM, RAM), solid-state storage media (e.g., flash drive), and/or other electronically readable storage media. The electronic storage 206 may include one or more virtual storage resources (e.g., cloud storage, a virtual private network, and/or other virtual storage resources). The electronic storage 206 may store software algorithms, information determined by a processor (e.g., processor 204), information received from external resources, information entered and/or selected via user interface 199, and/or other information that enables apparatus 10, 100 to function as described herein.

Using the robotic positioning apparatus 10, 100 and this semi-automatic method of stitching materials onto a prosthetic heart valve (for example) may provide increased precision, consistency, and efficiency while decreasing the amount of errors made and repetitive stress injuries suffered by operators. In some embodiments, the amount of time required to train an operator to become proficient in prosthetic heart valve production may also be decreased.

Figure 11:
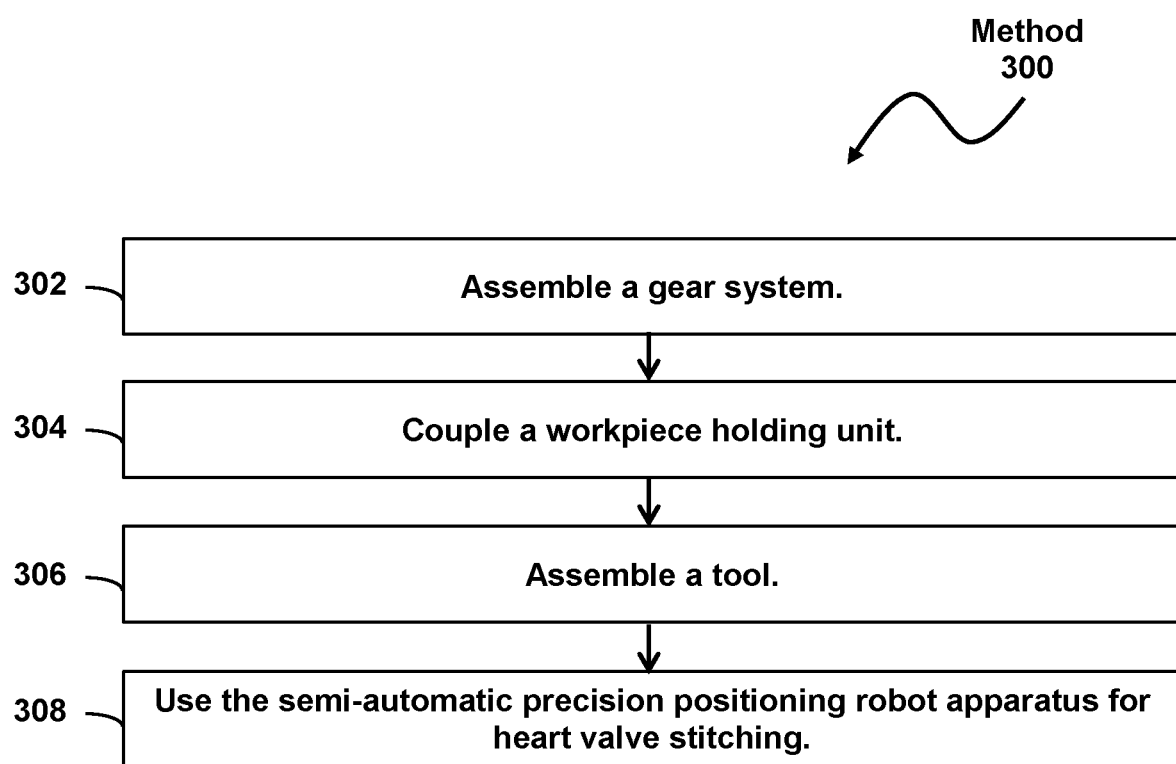
FIG. 11 illustrates a method for assembling and/or using the present robotic positioning apparatus.

FIG. 11 illustrates a method 300 for assembling a semi-automatic precision positioning robot apparatus and/or using the semi-automatic precision positioning robot apparatus. In some embodiments, method 300 may include operations related to using the semi-automatic precision positioning robot apparatus for heart valve stitching and/or other manufacturing activities. The operations of method 300 presented below are intended to be illustrative. In some embodiments, method 300 may be accomplished with one or more additional operations not described, and/or without one or more of the operations discussed. Additionally, the order in which the operations of method 300 are illustrated in FIG. 11 and described below is not intended to be limiting.

At an operation 302, a gear system may be assembled. In some embodiments, assembling the gear system may comprise assembling a plurality of gear chains, coupling a workpiece holding unit gear to the plurality of gear chains, and/or other operations. Assembling the plurality of gear chains may comprise, for an individual gear chain: providing a rotary actuator, coupling a gear shaft to the rotary actuator, coupling a worm wheel to the gear shaft, coupling a worm gear to the worm wheel, coupling an end gear to the worm gear, and/or other operations. In some embodiments, the workpiece holding unit gear may coupled to the end gear of each of the plurality of gear chains. In some embodiments, the end gear of each of the plurality of gear chains is a bevel gear. In some embodiments, the workpiece holding unit gear may be a bevel gear. In some embodiments, operation 302 may be performed with a gear system similar to or the same as gear system 50 (shown in FIGS. 5 and 6, and described herein).

At an operation 304, a workpiece holding unit may be coupled. The workpiece holding unit may be coupled to the workpiece holding unit gear and/or other components. In some embodiments, the gear system is configured to position a workpiece, by positioning the workpiece holding unit, relative to a tool. The tool may be configured to facilitate performance of a manufacturing operation on the workpiece. In some embodiments, operation 304 may be performed with a workpiece holding unit and/or a workpiece holding unit gear similar to or the same as workpiece holding unit 70 and/or bevel gear 72 (shown in FIGS. 5 and 6, and described herein).

In some embodiments, operation 302 and/or operation 304 may include assembling a support frame. Assembling the support frame may comprise providing a frame base, coupling frame posts to the frame base, coupling a frame cover coupled to the frame posts, and/or other operations. In some embodiments, operation 302 and/or 304 may include providing a plurality of linear actuators. An individual linear actuator may comprise at least one slide track, and/or other components. In some embodiments, operation 302 and/or 304 may include fixedly coupling the at least one slide track to the support frame, and coupling a slidable base to the at least one slide track. The slidable base may be configured to be actuated to move along the at least one slide track. The slidable base may have at least one movable platform receiving groove. The at least one moveable platform receiving groove may extend within the slidable base, for example, in an angled direction away from the slide track. In some embodiments, operation 302 and/or 304 may include coupling a moveable platform to the plurality of linear actuators; and coupling the gear system to the moveable platform.

At an operation 306, a tool may be assembled. Assembling the tool may comprise coupling a needle guide, a tensioning device, and/or other components to the semi-automatic precision positioning robot apparatus. The needle guide and the tensioning device may be configured to facilitate stitching in various applications, for one example, stitching associated with a medical device like a heart valve. In some embodiments, assembling the needle guide may comprise coupling a rotary actuator to the semi-automatic precision positioning robot apparatus. The rotary actuator may be configured to rotate the needle guide relative to the workpiece holding unit. Assembling the needle guide may comprise coupling a guidance structure to the rotary actuator. The guidance structure may be configured to removably receive and guide a stitching needle to a predetermined location on the medical device. In some embodiments, assembling the tensioning device comprises coupling a magnetic head to a base, and coupling the base to the semi-automatic precision positioning robot. The magnetic head may be configured to removably couple with a stitching thread. The base may be configured to position the magnetic head in proximity to the needle guide and the workpiece holding unit. In some embodiments, operation 306 may be performed with a needle guide and a tensioning device similar to or the same as needle guide 180 and tensioning device 187 (shown in FIGS. 7 and 8, and described herein).

At an operation 308, the semi-automatic precision positioning robot apparatus may be used for heart valve stitching and/or other operations. Operation 308 may include providing a guidance structure as part of the needle guide, and positioning the workpiece (e.g., valve) holding unit relative to the needle guide by actuating the plurality of gear chains to turn or move the workpiece (valve) holding unit (bevel) gear. Operation 308 may include aligning, by actuating the plurality of gear chains, a needle held by the needle guide to a stitch point on a heart valve held by the workpiece (valve) holding unit; and guiding, with the needle guide, completion of a stitch for the heart valve. Operation 308 may include positioning the workpiece (valve) holding unit by actuating at least one of the plurality of linear actuators such that at least one of the plurality of slidable bases moves in a direction along the slide track to position the workpiece (valve) holding unit. Operation 308 may include tensioning a stitching thread with the tensioning device of the semi-automatic precision positioning robot apparatus such that the thread has a desired amount of tension. In some embodiments, operation 308 may comprise determining a coordinate system, and one or both of: (1) positioning the workpiece (valve) holding unit relative to the needle guide by actuating the plurality of gear chains to turn or move the workpiece (valve) holding unit (bevel) gear based on the coordinate system; and (2) aligning, by actuating the plurality of gear chains, the needle held by the needle guide to the stitch point on the heart valve held by the workpiece (valve) holding unit based on the coordinate system. In some embodiments, operation 308 comprises displaying one or more images of the stitch point and/or other locations on the heart valve (or any other workpiece) on a display of the semi-automatic precision positioning robot apparatus. In some embodiments, operation 308 may be performed a system similar to or the same as system 10 and/or system 100 (shown in FIG. 1-10 and described herein).

Figure 12A:
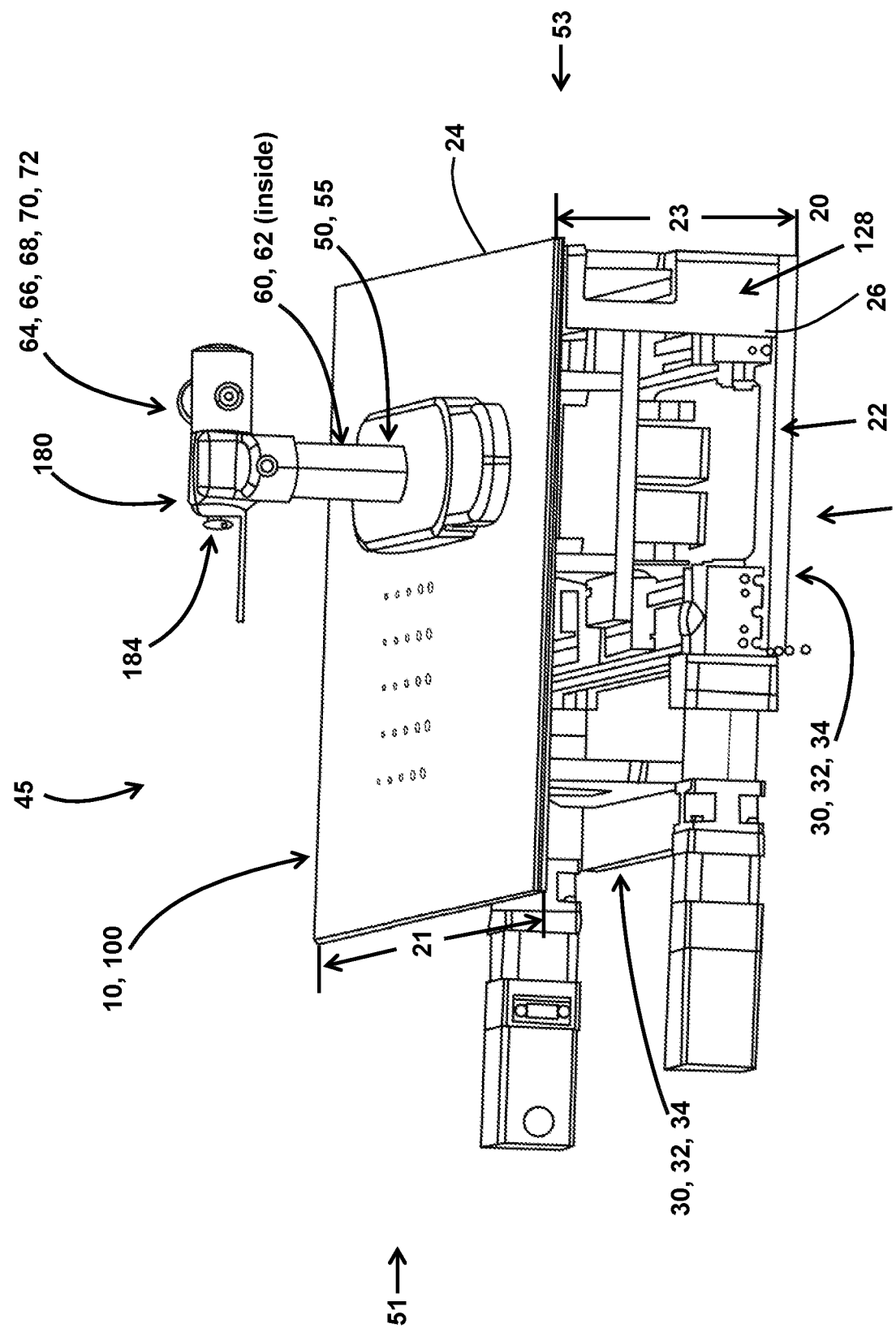
FIG. 12A illustrates a perspective view of an embodiment of the present robotic positioning apparatus.
Figure 12B:
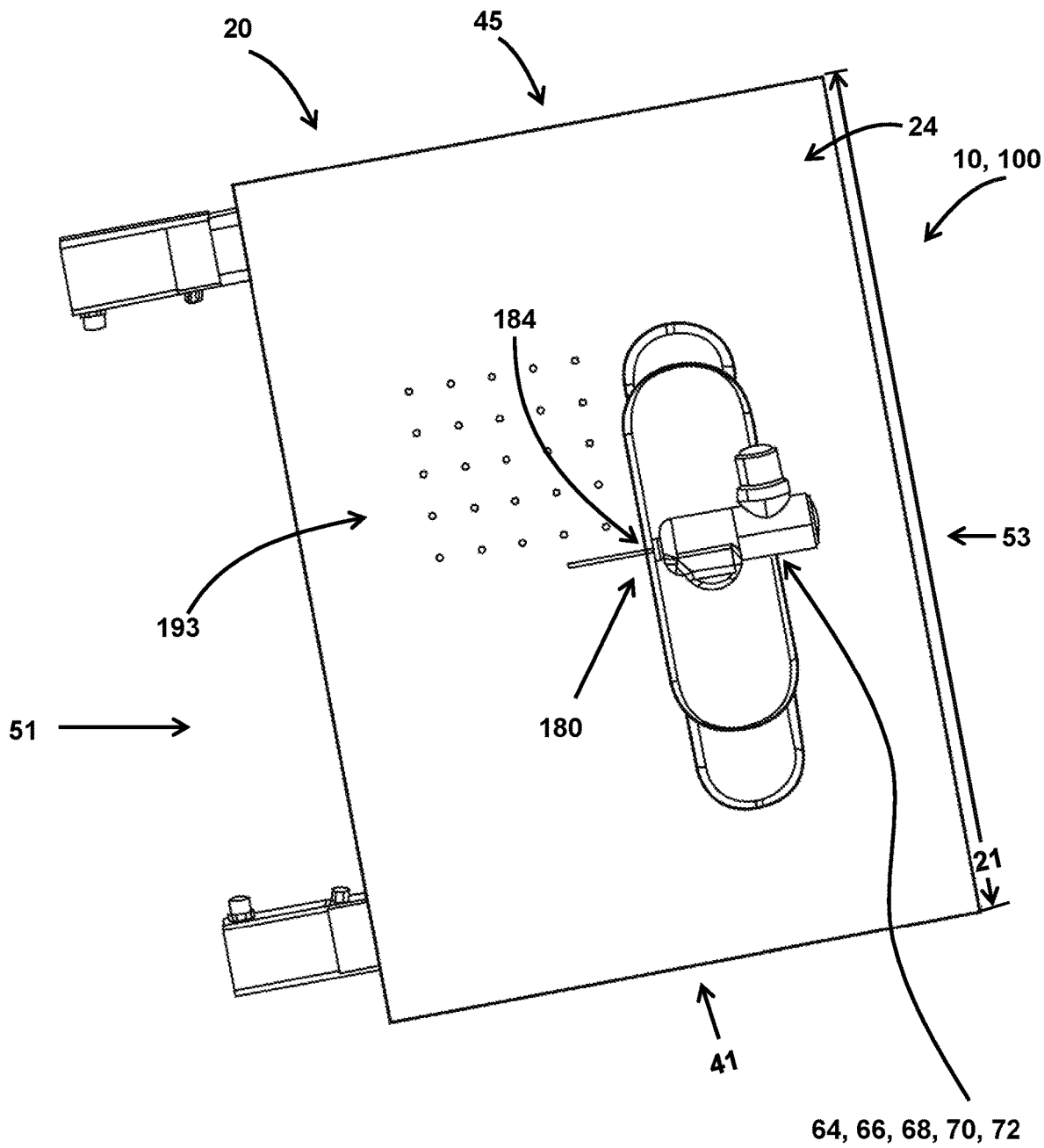
FIG. 12B illustrates a top view of the embodiment of the present robotic positioning apparatus illustrated in FIG. 12A.

FIG. 12A illustrates a perspective view of an embodiment of the robotic positioning apparatus 10, 100. FIG. 12B illustrates a top view of this embodiment of the robotic positioning apparatus 10, 100. FIGS. 12A and 12B are presented to compliment the previous figures described herein. FIG. 12A and/or FIG. 12B illustrate various components of apparatus 10, 100 including support frame 20, frame base 22, frame cover 24, frame posts 26, 28, linear actuators 30, slide tracks 32, slideable bases 34 and/or other components. FIG. 12A and/or 12B illustrate the relative positions of gear system 50, gear chains 55, rotary actuator 60, gear shaft 62, worm wheels 64, worm gears 66, bevel gears 68, work piece holding unit 70, bevel gear 72, and/or other components. FIGS. 12A and 12B also illustrate ends 41, 45, 51, and 53.

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

While the description above refers to particular embodiments, it will be understood that many modifications may be made without departing from the spirit thereof. The accompanying claims are intended to cover such modifications as would fall within the scope and sprit of embodiments herein.

The presently disclosed embodiments are, therefore, to be considered in all respects as illustrative and not restrictive.

All changes that come within the meaning of and range of equivalency of the claims are intended to be embraced therein.

The present techniques will be better understood with reference to the following enumerated embodiments:

1. A semi-automatic precision positioning robot apparatus, comprising: a gear system, the gear system comprising: a plurality of gear chains; a workpiece holding unit gear, wherein the workpiece holding unit gear is coupled to the plurality of gear chains; and a workpiece holding unit, wherein the workpiece holding unit is coupled to the workpiece holding unit gear; wherein the gear system is configured to position a workpiece, by positioning the workpiece holding unit, relative to a tool, the tool configured to facilitate performance of a manufacturing operation on the workpiece.

2. The apparatus of embodiment 1, further comprising the tool, the tool comprising a needle guide and a tensioning device configured to facilitate stitching.

3. The apparatus of embodiment 2, wherein the tool is configured to facilitate stitching associated with a medical device.

4. The apparatus of embodiment 2 or 3, wherein the needle guide comprises: a rotary actuator configured to rotate the needle guide relative to the workpiece holding unit; and a guidance structure configured to removably receive and guide a stitching needle to a predetermined location on the medical device; and wherein the tensioning device comprises: a magnetic head configured to removably couple with a stitching thread; and a base configured to position the magnetic head in proximity to the needle guide and the workpiece holding unit.

5. The apparatus of any of embodiments 1-4, wherein the plurality of gear chains individually comprise: a rotary actuator, a gear shaft, wherein the gear shaft is coupled to the rotary actuator, a worm wheel, wherein the worm wheel is coupled to the gear shaft, a worm gear, wherein the worm gear is coupled to the worm wheel, and an end gear, wherein the end gear is coupled to the worm gear; wherein the workpiece holding unit gear is coupled to the end gear of each of the plurality of gear chains.

6. The apparatus of embodiment 5, wherein the end gear further comprises a bevel gear.

7. The apparatus of any of embodiments 1-6, wherein the workpiece holding unit gear further comprises a bevel gear.

8. The apparatus of any of embodiments 1-7, further comprising: a support frame, wherein the support frame further comprises: a frame base, frame posts coupled to the frame base, and a frame cover coupled to the frame posts; a plurality of linear actuators, wherein an individual linear actuator comprises: at least one slide track, wherein the at least one slide track is fixedly coupled to the support frame; and a slidable base configured to be actuated to move along the at least one slide track, wherein the slidable base has at least one movable platform receiving groove, the at least one moveable platform receiving groove extending within the slidable base in an angled direction away from the slide track; and a moveable platform coupled to the plurality of linear actuators, wherein the gear system is coupled to the moveable platform.

9. A method for assembling a semi-automatic precision positioning robot apparatus, the method comprising: assembling a gear system, assembling the gear system comprising: assembling a plurality of gear chains; and coupling a workpiece holding unit gear to the plurality of gear chains; and coupling a workpiece holding unit to the workpiece holding unit gear; wherein the gear system is configured to position a workpiece, by positioning the workpiece holding unit, relative to a tool, the tool configured to facilitate performance of a manufacturing operation on the workpiece.

10. The method of embodiment 9, further comprising assembling the tool, assembling the tool comprising assembling a needle guide and a tensioning device, and coupling the needle guide and the tensioning device to the semi-automatic precision positioning robot apparatus, 11. The method of embodiment 10, wherein the needle guide and the tensioning device are configured to facilitate stitching associated with a medical device.

12. The method of embodiment 10 or 11, further comprising assembling the needle guide and the tensioning device, wherein assembling the needle guide comprises: coupling a rotary actuator to the semi-automatic precision positioning robot apparatus, the rotary actuator configured to rotate the needle guide relative to the workpiece holding unit; and coupling a guidance structure to the rotary actuator, the guidance structure configured to removably receive and guide a stitching needle to a predetermined location on the medical device; and wherein assembling the tensioning device comprises: coupling a magnetic head to a base, and coupling the base to the semi-automatic precision positioning robot, the magnetic head configured to removably couple with a stitching thread; and the base configured to position the magnetic head in proximity to the needle guide and the workpiece holding unit.

13. The method of any of embodiments 9-12, wherein assembling the plurality of gear chains comprises, for an individual gear chain: providing a rotary actuator, coupling a gear shaft to the rotary actuator, coupling a worm wheel to the gear shaft, coupling a worm gear to the worm wheel, and coupling an end gear to the worm gear; wherein the workpiece holding unit gear is coupled to the end gear of each of the plurality of gear chains.

14. The method of embodiment 13, wherein the end gear comprises a bevel gear.

15. The method of any of embodiments 9-14, wherein the workpiece holding unit gear further comprises a bevel gear.

16. The method of any of embodiments 9-15, further comprising: assembling a support frame, wherein assembling the support frame comprises: providing a frame base, coupling frame posts to the frame base, and coupling a frame cover to the frame posts; providing a plurality of linear actuators, wherein an individual linear actuator comprises: at least one slide track; fixedly coupling the at least one slide track to the support frame; coupling a slidable base to the at least one slide track, the slidable base configured to be actuated to move along the at least one slide track, wherein the slidable base has at least one movable platform receiving groove, the at least one moveable platform receiving groove extending within the slidable base in an angled direction away from the slide track; coupling a moveable platform to the plurality of linear actuators; and coupling the gear system to the moveable platform.

17. A method of using a semi-automatic precision positioning robot apparatus for heart valve stitching, comprising: providing a semi-automatic precision positioning robot apparatus comprising a gear system, wherein the gear system comprises: a plurality of gear chains, and a valve holding unit bevel gear, wherein the valve holding unit bevel gear is coupled to the plurality of gear chains; coupling a valve holding unit to the valve holding unit bevel gear; providing a needle guide, wherein the needle guide includes a needle guide rotary actuator and a guidance structure; positioning the valve holding unit relative to the needle guide by actuating the plurality of gear chains to turn or move the valve holding unit bevel gear; aligning, by actuating the plurality of gear chains, a needle held by the needle guide to a stitch point on a heart valve held by the valve holding unit; and guiding, with the needle guide, completion of a stitch for the heart valve.

18. The method of embodiment 17, wherein the semi-automatic precision positioning robot apparatus comprises: a support frame, wherein the support frame further comprises: a frame base, frame posts coupled to the frame base, and a frame cover coupled to the frame posts; a plurality of linear actuators, wherein the plurality of linear actuators further comprises: a slide track, wherein the slide track is fixedly attached to the support frame and a plurality of slidable bases that can be actuated to move along the slide track wherein the plurality of slidable bases has at least one movable platform receiving groove; and a moveable platform with at least one connecting portion that is received by the at least one movable platform receiving groove, wherein the gear system is mounted on the moveable platform; wherein the method further comprises: positioning the valve holding unit by actuating at least one of the plurality of linear actuators, wherein at least one of the plurality of slidable bases moves in a direction along the slide track to position the valve holding unit; and coupling the needle guide to the support frame.

19. The method of any of embodiments 17-18, further comprising: tensioning a stitching thread with a tensioning device of the semi-automatic precision positioning robot apparatus such that the thread has a desired amount of tension.

20. The method of embodiment 19, wherein the tensioning device comprises: a suture tensioning arm with a magnetic end; and a metal disc magnetically attachable to the magnetic end.

21. The method of any of embodiments 17-20, further comprising determining a coordinate system, and one or both of: (1) positioning the valve holding unit relative to the needle guide by actuating the plurality of gear chains to turn or move the valve holding unit bevel gear based on the coordinate system; and (2) aligning, by actuating the plurality of gear chains, the needle held by the needle guide to the stitch point on the heart valve held by the valve holding unit based on the coordinate system.

22. The method of any of embodiments 17-21, further comprising displaying one or more images of the stitch point on the heart valve on a display of the semi-automatic precision positioning robot apparatus.

We claim:

1. The semi-automatic precision positioning robot apparatus comprising:
a movable platform for supporting a workpiece;
a plurality of linear actuators, wherein each individual linear actuator comprises:
  a slide track; and
  a slidable base configured to be actuated to move along the slide track, wherein the slidable base has a movable platform receiving groove, the moveable platform receiving groove extending within the slidable base in an angled direction away from the slide track; and
wherein the moveable platform is coupled to the plurality of linear actuators, the movable platform including connecting portions, each of the connecting portions received within a corresponding one of the moveable platform receiving grooves,
wherein movement of the slidable bases along their corresponding slide track results in a corresponding movement of the connecting portions within their corresponding moveable platform receiving groove.

2. The semi-automatic precision positioning robot apparatus of claim 1, wherein the movable platform moves in a direction transverse to a longitudinal axis of at least one of the moveable platform receiving grooves.

3. The semi-automatic precision positioning robot apparatus of claim 1, wherein the movable platform moves in a direction perpendicular to a longitudinal axis of at least one of the slide tracks.

4. The semi-automatic precision positioning robot apparatus of claim 1, wherein at least one of the movable platform receiving grooves extends within their corresponding slidable base at an increasing angle with respect to a longitudinal axis of the corresponding slide track.

5. The semi-automatic precision positioning robot apparatus of claim 1, wherein each of the connecting portions includes a wheel sized and configured to be received within the corresponding movable platform receiving groove, wherein the wheel is movable within the platform receiving grooves.

6. The semi-automatic precision positioning robot apparatus of claim 1, including a workpiece holding unit coupled to the movable platform.

7. The semi-automatic precision positioning robot apparatus of claim 6, wherein movement of the movable platform is configured to position a workpiece coupled to the workpiece holding unit relative a tool, the tool configured to facilitate performance of a manufacturing operation on the workpiece.

8. The semi-automatic precision positioning robot apparatus of claim 7, wherein the tool comprises a needle guide.

9. The semi-automatic precision positioning robot apparatus of claim 8, wherein the needle guide comprises:
a rotary actuator configured to rotate the needle guide relative to the workpiece holding unit; and
wherein the tool further comprises a tensioning device including:
  a magnetic head configured to removably couple with a stitching thread; and
  a base configured to position the magnetic head in proximity to the needle guide and the workpiece holding unit.

10. The semi-automatic precision positioning robot apparatus of claim 1, further comprising:
a support frame, wherein the support frame further comprises:
a frame base;
frame posts coupled to the frame base, and
a frame cover coupled to the frame posts;
wherein the slide track of each of the plurality of linear actuators is fixedly coupled to the support frame.

11. A method for assembling a semi-automatic precision positioning robot apparatus, the method comprising:
assembling a support frame, wherein assembling the support frame comprises:
  providing a frame base,
  coupling frame posts to the frame base, and
  coupling a frame cover to the frame posts;
providing a plurality of linear actuators, wherein an individual linear actuator comprises: at least one slide track;
fixedly coupling the at least one slide track to the support frame;
coupling a slidable base to the at least one slide track, the slidable base configured to be actuated to move along the at least one slide track, wherein the slidable base has at least one movable platform receiving groove, the at least one moveable platform receiving groove extending within the slidable base in an angled direction away from the at least one slide track;

coupling a moveable platform to the plurality of linear actuators; and coupling a workpiece holding unit to the moveable platform, wherein the movable platform is configured to position a workpiece, by positioning the workpiece holding unit, relative to a tool, the tool configured to facilitate performance of a manufacturing operation on the workpiece.

12. The method of claim 11, wherein the movable platform includes connecting portions extending from a first and second side edge of the movable platform;

wherein coupling the moveable platform to the plurality of linear actuators further comprises:

receiving the connection portions within a corresponding one of the movable platform receiving grooves such that the connecting portions are coupled to and moveable within the movable platform receiving grooves.

13. The method of claim 11, further comprising assembling the tool, assembling the tool comprising assembling a needle guide and coupling the needle guide to the semi-automatic precision positioning robot apparatus.

14. The method of claim 13, wherein assembling the needle guide comprises:

coupling a rotary actuator to the semi-automatic precision positioning robot apparatus, the rotary actuator configured to rotate the needle guide relative to the workpiece holding unit; and coupling the needle guide to the rotary actuator.

15. The method of claim 14, wherein assembling the tool further comprises:

assembling a magnetic tensioning device and coupling the magnetic tensioning device to the semi-automatic precision positioning robot apparatus.

16. The method of claim 15, wherein assembling the magnetic tensioning device comprises:

coupling a magnetic head to a base, and coupling the base to the semi-automatic precision positioning robot, the magnetic head configured to removably couple with a stitching thread; and the base configured to position the magnetic head in proximity to the needle guide and the workpiece holding unit.

17. The method of claim 15, further comprising:

tensioning a stitching thread with the magnetic tensioning device of the semi-automatic precision positioning robot apparatus such that the thread has a desired amount of tension.

18. The method of claim 14, further comprising establishing a coordinate system based on one or both of:

(1) positioning the workpiece holding unit relative to the needle guide by actuating the plurality of linear actuators to move the movable platform and as a result the workpiece holding unit; and (2) positioning the needle guide relative to the workpiece holding unit by actuating the rotary actuator to rotate the needle guide.

* * * * *